United States Patent
Baran et al.

(10) Patent No.: US 10,105,094 B2
(45) Date of Patent: Oct. 23, 2018

(54) SUPPLEMENTARY DEVICE FOR A MANUALLY OPERABLE INJECTION DEVICE

(71) Applicant: SANOFI-AVENTIS DEUTSCHLAND GMBH, Frankfurt am Main (DE)

(72) Inventors: André Baran, Steinfurt (DE); Kay Behrendt, Bad Bentheim (DE); Erich Rittenbacher, Vienna (AT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/373,134

(22) PCT Filed: Feb. 8, 2013

(86) PCT No.: PCT/EP2013/052504
§ 371 (c)(1),
(2) Date: Jul. 18, 2014

(87) PCT Pub. No.: WO2013/120773
PCT Pub. Date: Aug. 22, 2013

(65) Prior Publication Data
US 2015/0025470 A1    Jan. 22, 2015

Related U.S. Application Data

(60) Provisional application No. 61/605,455, filed on Mar. 1, 2012.

(30) Foreign Application Priority Data

Feb. 13, 2012    (EP) .................................... 12155196

(51) Int. Cl.
*A61B 5/00*    (2006.01)
*A61M 5/178*    (2006.01)
(Continued)

(52) U.S. Cl.
CPC ........ *A61B 5/4839* (2013.01); *A61B 5/14532* (2013.01); *A61M 5/003* (2013.01);
(Continued)

(58) Field of Classification Search
CPC ................... A61M 5/24; A61M 5/002; A61M 2005/3126; A61M 5/31525; A61M 5/003;
(Continued)

(56) References Cited

U.S. PATENT DOCUMENTS 533,575 A    2/1895    Wilkens
3,080,866 A  *  3/1963    Friedman .............. A61J 1/2089
                                                 604/125
(Continued)

FOREIGN PATENT DOCUMENTS

EP        0937471        8/1999
EP        0937476        8/1999
(Continued)

OTHER PUBLICATIONS

International Search Report for Int. App. No. PCT/EP2013/052504, completed Mar. 12, 2013.

*Primary Examiner* — Lauren P Farrar
(74) *Attorney, Agent, or Firm* — Fish & Richardson P.C.

(57) ABSTRACT

The present invention relates to a supplementary device a supplementary device for a manually operable injection device. The supplementary device has a body defining a passage through which an injection device is slidable, and a securing unit to secure the body to the injection device in the specific position when the injection device is received through the passage.

20 Claims, 16 Drawing Sheets

(51) Int. Cl.
  *A61M 5/315*     (2006.01)
  *A61B 5/145*     (2006.01)
  *A61M 5/24*      (2006.01)
  *A61M 5/31*      (2006.01)
  *A61M 5/00*      (2006.01)

(52) U.S. Cl.
  CPC .............. *A61M 5/178* (2013.01); *A61M 5/24* (2013.01); *A61M 5/31525* (2013.01); *A61B 5/14503* (2013.01); *A61M 5/002* (2013.01); *A61M 2005/3126* (2013.01); *A61M 2205/3306* (2013.01); *A61M 2205/3375* (2013.01); *A61M 2205/50* (2013.01); *A61M 2205/502* (2013.01); *A61M 2205/52* (2013.01); *A61M 2205/581* (2013.01); *A61M 2209/04* (2013.01)

(58) Field of Classification Search
  CPC ...... A61M 2205/50; A61M 2205/3375; A61M 2205/3306; A61M 2205/502; A61M 2205/581; A61M 2205/52; A61M 2209/04; A61B 5/4839; A61B 5/14532; A61B 5/14503
  See application file for complete search history.

(56) References Cited

U.S. PATENT DOCUMENTS

| | | |
|---|---|---|
| 5,226,895 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0011506 A1* | 1/2006 | Riley .................. A61B 19/026 206/570 |
| 2006/0153693 A1 | 7/2006 | Fiechter et al. |
| 2008/0132839 A1* | 6/2008 | Strobl ..................... A61M 5/32 604/131 |
| 2009/0275916 A1 | 11/2009 | Harms et al. |
| 2010/0145656 A1 | 6/2010 | Koehler et al. |
| 2010/0280369 A1* | 11/2010 | Bruce ............... A61M 5/14546 600/432 |

FOREIGN PATENT DOCUMENTS

| | | | |
|---|---|---|---|
| JP | 2001-509426 A | 7/2001 | |
| JP | 2007-512109 A | 5/2007 | |
| JP | 2008-142512 A | 6/2008 | |
| WO | 99/02210 | 1/1999 | |
| WO | 99/38554 | 8/1999 | |
| WO | 01/10484 | 2/2001 | |
| WO | 2005/053771 A2 | 6/2005 | |
| WO | 2009/024562 | 2/2009 | |
| WO | 2010/037828 | 4/2010 | |
| WO | WO 2010037828 A1 * | 4/2010 | ........ A61M 5/31525 |
| WO | 2010/098927 | 9/2010 | |
| WO | 2010/128493 A2 | 11/2010 | |
| WO | 2011/117212 | 9/2011 | |

\* cited by examiner

SUPPLEMENTARY DEVICE FOR A MANUALLY OPERABLE INJECTION DEVICE

CROSS REFERENCE TO RELATED APPLICATIONS

The present application is a U.S. National Phase application pursuant to 35 U.S.C. § 371 of International Application No. PCT/EP2013/052504 filed Feb. 8, 2013,which claims priority to European Patent Application No. 12155196.4 filed Feb. 13, 2012 and U.S. Provisional Patent Application No. 61/605,455, filed Mar. 1, 2012. The entire disclosure contents of these applications are herewith incorporated by reference into the present application.

TECHNICAL FIELD

The present invention relates to an apparatus for supplementing a medical device configured to eject a medicament. In particular, the present invention relates to a supplementary device for a manually operable injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen.

To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outer normal operating conditions, and to communicate data relating to the measured values to an external device for further data processing.

The control circuit of the medical device described in WO 2009/024562 can thus be used with a series of pre-filled disposable injection devices, but the requirement that the RFID unit with the value sensor is contained in the medicament container of the pre-filled disposable injection devices significantly increases the costs of the pre-filled disposable injection device.

It has been described, for instance in WO 2011/117212 to provide a supplementary device comprising a mating unit for releasably attaching the device to an injection device. The device includes a camera and is configured to perform optical character recognition (OCR) on captured images visible through a dosage window of the injection device, thereby to determine a dose of medicament that has been dialled into the injection device.

SUMMARY

It is thus inter alia an object of the present invention to provide a supplementary device for a manually operable injection device.

According to a first aspect of embodiments of the present invention, there is provided a supplementary device for a manually operable injection device, the supplementary device comprising a body defining a passage through which an injection device is slidable, and a securing unit configured to secure the body to the injection device in the specific position when the injection device is received through the passage.

The passage may be an elongate bore formed in the body.

The securing unit may comprise at least two clamping surfaces. The securing unit may be configured to receive the injection device between the clamping surfaces when the injection device is received through the collar and to bias at least one of the clamping surfaces towards the other clamping surface or surfaces to clamp the injection device between the clamping surfaces.

The securing unit may comprise at least two securing members which are spaced apart to receive the injection device therebetween. Each securing member may define a clamping surface.

The supplementary device may further comprise a biasing element configured to bias at least one of the securing members towards other securing member or members.

The biasing element may be configured to bias each of the securing members towards each other.

The biasing element may be a collar extending over the securing members. The collar may have a biasing section configured to act on at least one of the securing members to releasably bias at least one of the clamping surfaces towards the other clamping surface or surfaces.

The biasing section may be tapered.

The biasing section of the collar may be threadingly engaged with the securing members.

The threaded engagement may be tapered.

The at least two securing members may be arms extending from the body.

The arms may be resilient and may be biased away from each other.

The securing unit may comprise an engaging element configured to engage with a cap retaining protrusion on the injection device when the body is disposed in a specific position relative to an outer surface of the injection device.

The securing unit may comprise an actuating member pivotably mounted in the body having at least one engaging element, the engaging element being configured to engage in an indent on the injection device when the body is disposed in a specific position relative to an outer surface of the injection device and the actuating member is pivoted towards the body.

The supplementary device may further comprise a locating unit configured to locate the body in a specific position relative to an outer surface of the injection device.

The locating unit may comprise a locating recess in the body. The locating recess may be configured to mate with a locating rib on the injection device.

The locating unit may comprise a locating step configured to mate with a shoulder formed on the outer surface of the injection device.

A passageway may be formed in the body to receive the injection device therethrough, the locating step being formed in an inner surface of the passageway.

The locating step may be formed by the securing unit.

The locating unit may comprise a guide slot, the guide slot being configured to mate with a cap retaining protrusion on the injection device.

The supplementary device may further comprise an auxiliary cap retaining element configured to releasably retain a cap received over an end of the injection device when the supplementary device is secured to the injection device.

The supplementary device may further comprise an optical reading arrangement and wherein the optical reading arrangement is directed at a display of the injection device when the body is mounted to the injection device in a specific position relative to an outer surface of the injection device.

According to another aspect of embodiments of the invention, there is provided a kit comprising an injection device and a supplementary device.

Embodiments of the invention will now be described, by way of example only, with reference to the accompanying drawings.

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1:
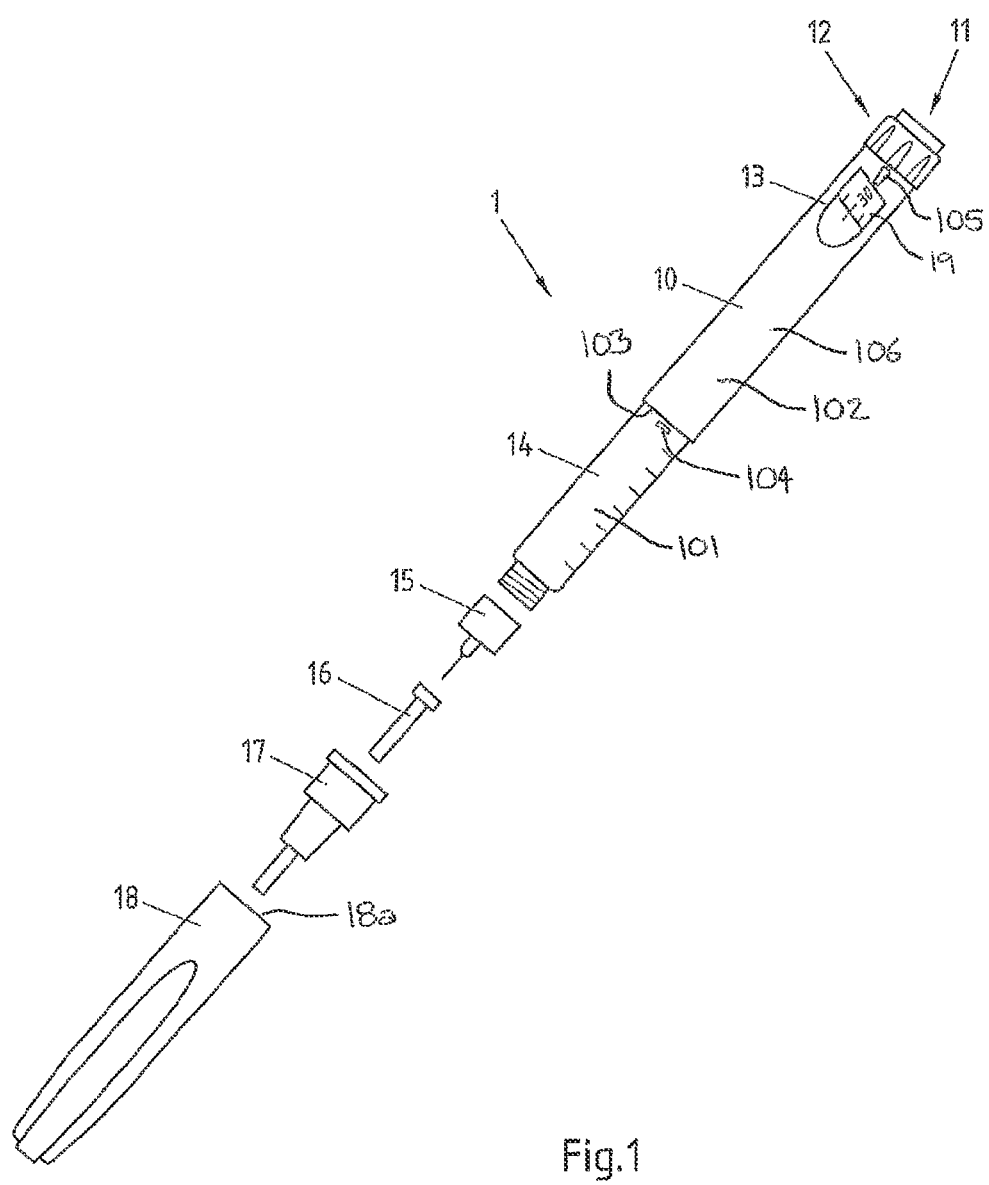
FIG. 1: an exploded view of an injection device.

FIG. 1 is an exploded view of an injection device 1, which may for instance represent Sanofi's Solostar® insulin injection pen.

The injection device 1 of FIG. 1 is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning a dosage knob 12, and the selected dose is then displayed via a dosage window or display 13, for instance in multiples of so-called International Units (IU), wherein one IU is the biological equivalent of about 45.5 micrograms of pure crystalline insulin (1/22 mg). An example of a selected dose displayed in dosage window or display 13 may for instance be 30 IUs, as shown in FIG. 1. It should be noted that the selected dose may equally well be displayed differently, for instance by an electronic display. It will be understood that dosage window relates to the section of the injection device through or on which the selected dosage is visible.

A label (not shown) is provided on the housing 10. The label includes information about the medicament included within the injection device, including information identifying the medicament. The information identifying the medicament may be in the form of text. The information identifying the medicament may also be in the form of a shading or pattern. The information identifying the medicament may also be in the form of a colour. The information identifying the medicament may also be encoded into a barcode, QR code or the like.

Turning the dosage knob 12 causes a mechanical click sound to provide acoustical feedback to a user. The numbers displayed in dosage display 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

The housing 10 of the injection device 1 comprises a front section 101 and a rear section 102. The needle 15 is affixed to the front end of the front section 101 and the dosage knob 12 extends from the rear end of the rear section 102. The front section 101 has a smaller diameter than the rear section 102 of the injection device housing 10. A shoulder 103 is defined between the front section 101 and the rear section 102. The shoulder 103 extends circumferentially around the housing 10.

The cap 18 extends over the front section 101. The cap 18 covers the front section 101 and a rim 18a of the cap 18 locates against the shoulder 103.

Two cap retaining protrusions 104 are formed on the outer surface of the front section 101 of the housing 10 of the injection device 1. The cap retaining protrusions 104 are disposed proximate to, but spaced from, the shoulder 103. The protrusions 104 locate over one or more retaining elements (not shown) formed on the inner surface of the cap 18 to retain the cap 18 in position over the front section 101. Alternatively, the cap retaining protrusions 104 locate in a corresponding diametrically extending recess (not shown) formed on the inner surface of the cap 18. The height of each protrusion 104, that is in a radial direction of the longitudinal axis of the injection device 1, is less than the height of the shoulder 103 between the front and rear sections 101, 102. The two protrusions are disposed diametrically opposite each other. The number of protrusions is not limited thereto, and the protrusions are dispersed circumferentially around the front section 101.

The injection device 1 further comprises additional elements. A rib 105 protrudes from an outer surface 106 of the injection device 1. The rib 105 acts as an alignment element for locating the body in a specific position relative to the outer surface 106 of the injection device 1. The rib 105 upstands from the outer surface 106 of the injection device 1 between the dosage window 13 and the dosage knob 12. In this example, the rib 105 extends for the whole of the distance between the display window 13 and the dosage knob 12. In other examples, the rib is shorter. The dosage knob 12 is disposed on the rear section 102 of the injection device housing 10. The rib 105 is elongate and extends parallel to the longitudinal axis of the injection device 1. The height of the rib 105, that is the distance between the outer surface of the rear section 102 and a distal edge 107 (refer to FIG. 9) of the rib 105 is greater at the end that is adjacent the dosage knob 12 and tapers down to a zero height at the junction with the display window 13.

Left and right indents 108 (refer to FIG. 16) are formed in the outer surface 106 of the injection device 1. The two indents 108 are formed in the rear section 102. Each indent 108 is formed proximate to the rear end of the injection device housing 10. The indents are formed generally diametrically opposite to each other on left and right sides of the injection device 1. The indents have chamfered sides.

Figure 2A:
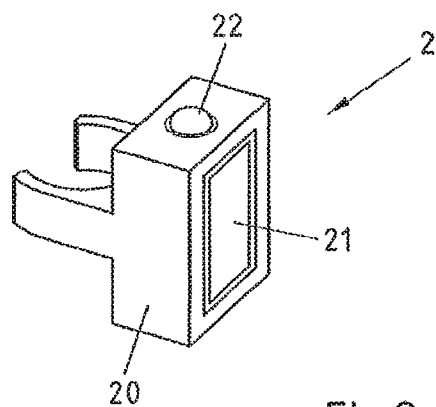
FIG. 2a: a schematic illustration of a supplementary device to be releasably attached to the injection device of FIG. 1 according to an embodiment of the present invention.

FIG. 2a is a schematic illustration of an embodiment of a supplementary device 2 to be releasably attached to injection device 1 of FIG. 1. Supplementary device 2 comprises a housing 20 with a mating unit configured to embrace the housing 10 of injection device 1 of FIG. 1, so that supplementary device 2 sits tightly on housing 10 of injection device 1, but is nevertheless removable from injection device 1, for instance when the injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises three user input transducers, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
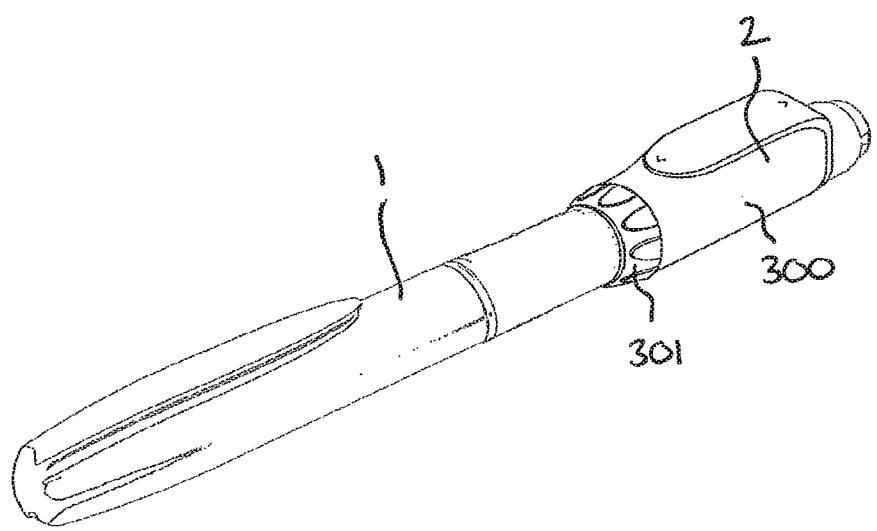
FIG. 2b: a perspective view of the supplementary device of FIG. 2a releasably attached to the injection device of FIG. 1.

FIG. 2b shows a view of the supplementary device 2 with the arrangement of the mating unit and housing shown in greater detail. The supplementary device 2 is shown mounted to the injection device 1 in FIG. 2b.

The housing 20 of the supplementary device 2 has a body 300 and a securing unit 301. The body 300 is elongate. A passage 302 extends through the body 300 from a front end 304 to a rear end 305. The passage 302 is configured to slidably receive the injection device therethrough. In the present arrangement, the passage 302 is a cylindrical bore formed through the body 300. The passage 302 is dimensioned to receive a rear section 102 of the injection device therethrough. In the present arrangement, the injection device 1 is cylindrical and the passage 302 has a diameter which is slightly greater than the diameter of the rear section 102 of the injection device 1 so that the injection device 1 is slidable therealong. The securing unit 301 is disposed at the front end 304 of the body 300.

The securing unit 301 comprises a collar 303. The collar 303 is rotatably mounted to the body 300. The collar 303 extends from the front end 304. The collar 303 is movable between an retracted position and a secured position to secure the supplementary device to the injection device, as will become apparent hereinafter. The injection device 1 is receivable through the collar 303 when the device is received in the passage 302 in the body 300.

The collar 303 and channel 330 form part of a locating arrangement or locating Unit. The locating unit is configured to locate the body in a specific position relative to the outer surface 106 of the injection device 1. The locating unit forms part of the mating unit configured to embrace the housing 10 of injection device 1 to maintain the supplementary device in a specific position on the injection device 1.

The supplementary device 2 further comprises a securing arrangement or unit configured to releasably mount the body to the injection device 1. The collar 303 also forms part of the securing unit. The securing unit form part of the mating unit.

The features that contribute to correct location or alignment of the supplementary device 2 on the injection device 1 can be termed a locating arrangement or locating unit. The features that contribute to securing of the supplementary device 2 to the injection device 1 can be termed a securing unit or securing arrangement.

Figure 3A:
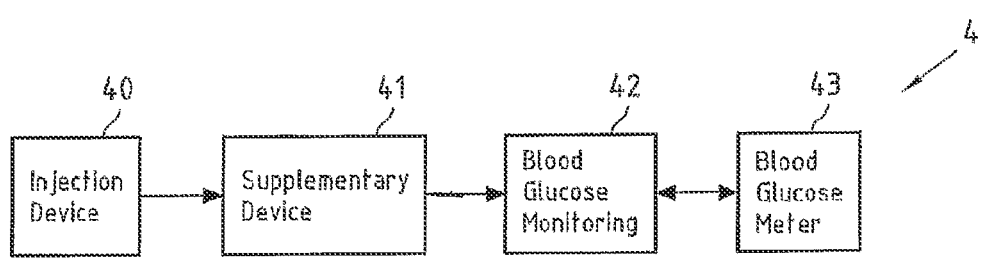
FIGS. 3A and 3b: possible distributions of functions among devices when using a supplementary device (such as the supplementary devices of FIGS. 2a and 2b) together with an injection device.
Figure 3B:
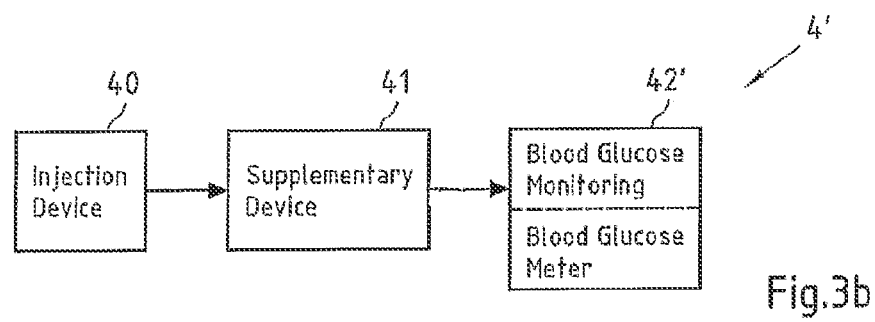

FIGS. 3A and 3b show possible distributions of functions among devices when using a supplementary device (such as the supplementary devices of FIGS. 2a and 2b) together with an injection device.

In constellation 4 of FIG. 3a, the supplementary device 41 (such as the supplementary devices of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as a desktop computer, personal digital assistant, mobile phone, tablet computer, notebook, netbook or ultrabook) keeps a record of the injections a patient has received so far (based on the ejected doses, for instance by assuming that the ejected doses and the injected doses are the same, or by determining the injected doses based on the ejected doses, for instance be assuming that a pre-defined percentage of the ejected dose is not completely received by the patient). Blood glucose monitoring system 42 may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42. Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionalities of injection device 40 and supplementary device 41 of FIG. 3a are not affected by this modification. Also the functionality of blood glucose monitoring system 42 and blood glucose meter 43 combined into blood glucose monitoring system 42' are basically unchanged, apart from the fact that both are now comprised in the same device, so that external wired or wireless communication between these devices is no longer necessary. However, communication between blood glucose monitoring system 42 and blood glucose meter 43 takes place within system 42'.

Figure 4:
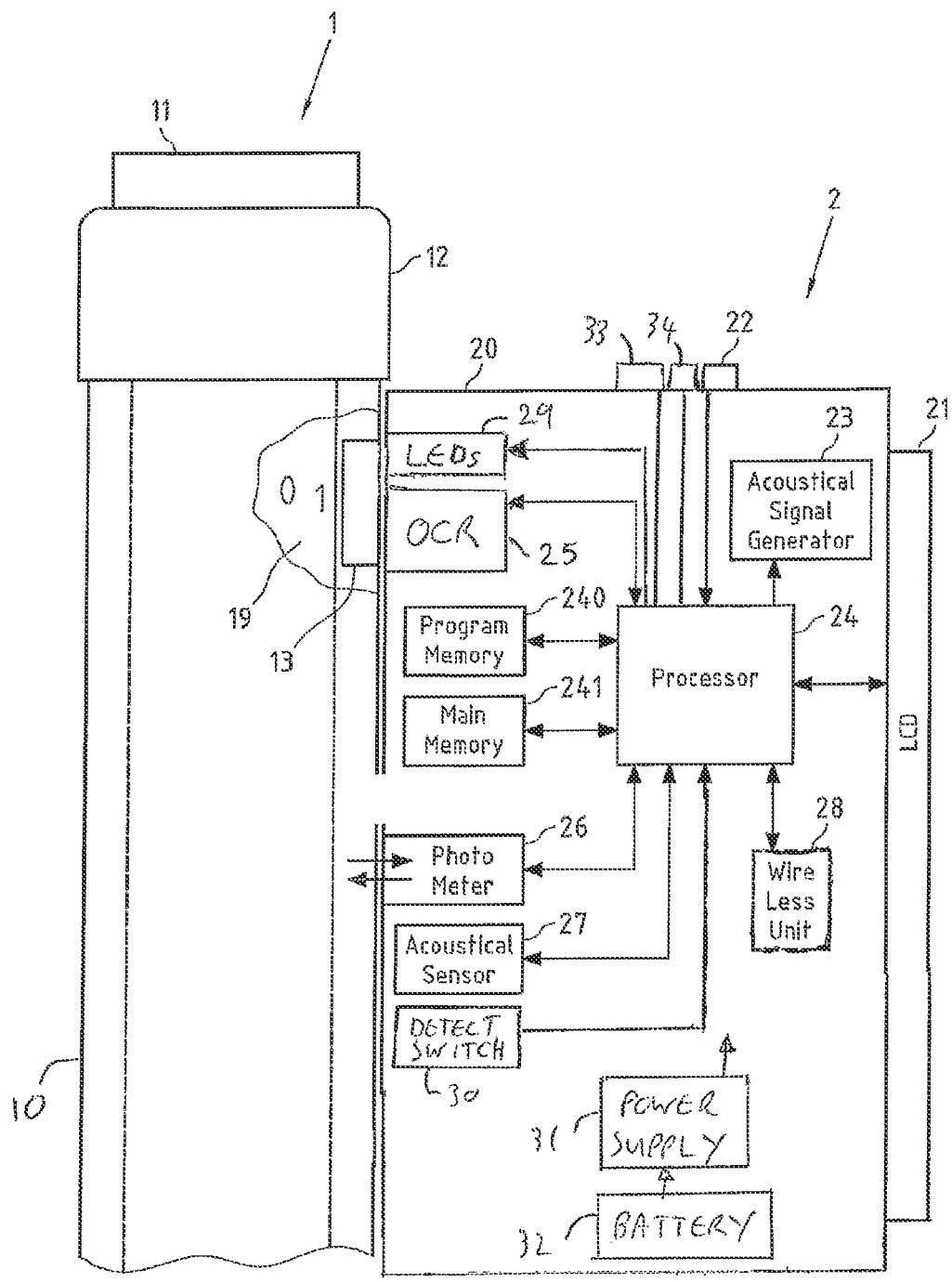
FIG. 4: a schematic view of the supplementary device of FIG. 2 in a state where it is mounted to the injection device of FIG. 1.

FIG. 4 shows a schematic view of the supplementary device 2 of FIG. 2a in a state where it is attached to injection device 1 of FIG. 1.

With the housing 20 of supplementary device 2, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In an example embodiment, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. The buttons 22, 33, 34 may be any suitable form of user input transducers, for instance mechanical switches, capacitive sensors or other touch sensors.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by way of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens (e.g. an aspheric lens) leading to a magnification (e.g. a magnification of more than 3:1).

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance a expiration date).

Processor 24 further controls (and/or receives signals from) an acoustic sensor 27, which is configured to sense sounds produced by injection device 1. Such sounds may for instance occur when a dose is dialled by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1.

A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 5A:
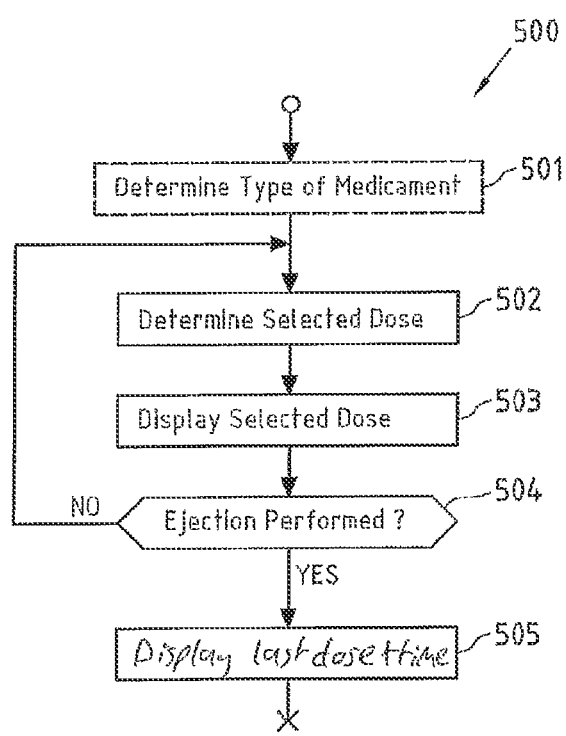
FIG. 5a: a flowchart of a method used in various embodiments.
Figure 5B:
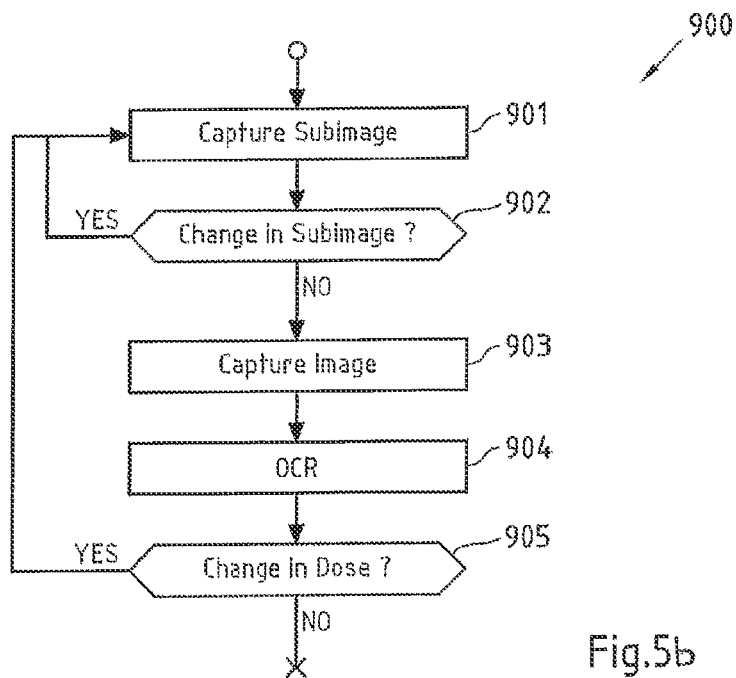
FIG. 5b: a flowchart of a further method used in various embodiments.
Figure 5C:
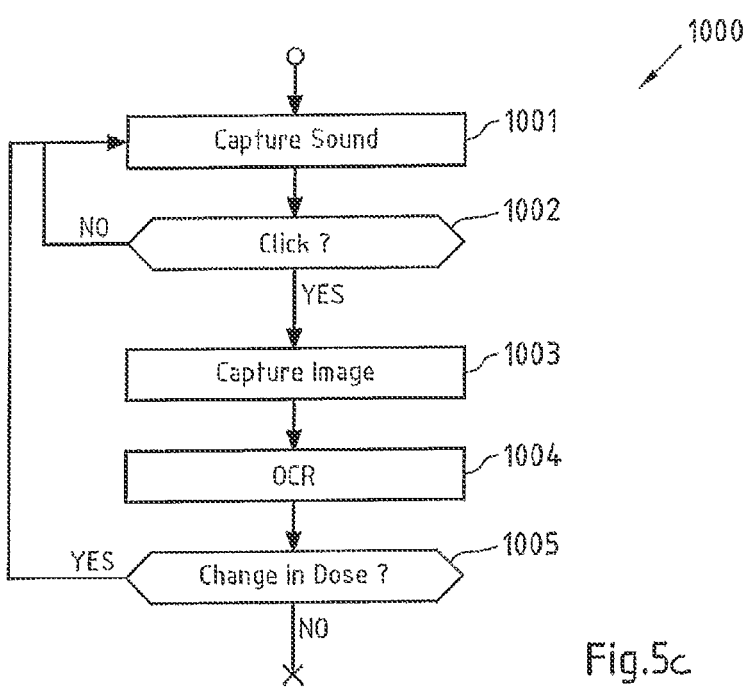
FIG. 5c: a flowchart of another method used in various embodiments.

FIGS. 5*a*-5*c* are flowcharts of embodiments of methods according to the present invention. These methods may for instance be performed by processor 24 of supplementary device 2 (see FIGS. 2*b* and 4), but also by a processor of supplementary device 3 of FIG. 2*b*, and may for instance be stored in program memory 240 of supplementary device 2, which may for instance take the shape of tangible storage medium 60 of FIG. 6.

FIG. 5*a* shows method steps that are performed in scenarios as shown in FIGS. 3*a* and 3*b*, where information read by supplementary device 41 from injection device 40 is provided to blood glucose monitoring system 42 or 42' without receiving information back from blood glucose monitoring system 42 or 42'.

The flowchart 500 starts for instance when the supplementary device is turned on or is otherwise activated. In a step 501, a type of medicament, for example insulin, provided by the injection device is determined, for instance based on colour recognition or based on recognition of a code printed on injection device or a component thereof as already described above. Detection of the type of medicament may not be necessary if a patient always takes the same type of medicament and only uses an injection device with this single type of medicament. Furthermore, determination of the type of medicament may be ensured otherwise (e.g. by the key-recess pair shown in FIG. 4 that the supplementary device is only useable with one specific injection device, which may then only provide this single type of medicament).

In a step 502, a currently selected dose is determined, for instance by OCR of information shown on a dosage window of injection device as described above. This information is then displayed to a user of the injection device in a step 503.

In a step 504, it is checked if an ejection has taken place, for instance by sound recognition as described above. Therein, a prime shot may be differentiated from an actual injection (into a creature) either based on respectively different sounds produced by the injection device and/or based on the ejected dose (e.g. a small dose, for instance less than a pre-defined amount of units, e.g. 4 or 3 units, may be considered to belong to a prime shot, whereas larger doses are considered to belong to an actual injection).

If an ejection has taken place, the determined data, i.e. the selected dose and—if applicable—the type of medicament (e.g. insulin), is stored in the main memory 241, from where it may later be transmitted to another device, for instance a blood glucose monitoring system. If a differentiation has been made concerning the nature of the ejection, for instance if the ejection was performed as a prime shot or as an actual injection, this information may also be stored in the main memory 241, and possibly later transmitted. In the case of an injection having been performed, at step 505 the dose is displayed on the display 21. Also displayed is a time since the last injection which, immediately after injection, is 0 or 1 minute. The time since last dose may be displayed intermittently. For instance, it may be displayed alternately with the name or other identification of the medicament that was injected, e.g. Apidra or Lantus.

If ejection was not performed at step 504, steps 502 and 503 are repeated.

After display of the delivered dose and time data, the flowchart 500 terminates.

FIG. 5*c* shows in more detail exemplary method steps that are performed when the selected dose is determined based on the use of optical sensors only. For instance, these steps may be performed in step 502 of FIG. 5*a*.

In a step 901, a sub-image is captured by an optical sensor such as optical sensor 25 of supplementary device 2. The captured sub-image is for instance an image of at least a part of the dosage window 13 of injection device 1, in which a currently selected dose is displayed (e.g. by way of numbers and/or a scale printed on the sleeve 19 of injection device 1, which is visible through the dosage window 13). For instance, the captured sub-image may have a low resolution and/or only show a part of the part of sleeve 19 which is visible through dosage window 13. For instance, the captured sub-image either shows the numbers or the scale printed on the part of sleeve 19 of injection device 1 which is visible through dosage window 13. After capturing an image, it is, for instance, further processed as follows:

Division by a previously captured background image;
Binning of the image(s) to reduce the number of pixels for further evaluations;
Normalization of the image(s) to reduce intensity variations in the illumination;
Sheering of the image(s); and/or
Binarization of the image(s) by comparing to a fixed threshold.

Several or all of these steps may be omitted if applicable, for instance if a sufficiently large optical sensor (e.g. a sensor with sufficiently large pixels) is used.

In a step 902, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns. Steps 901 and 902 may correspond to a detection of a change in the captured image.

If it is determined in step 902 that there is a change in the sub-image, step 901 is repeated. Otherwise in a step 903, an image is captured by an optical sensor such as optical sensor 25 of supplementary device 2. The captured image is for instance an image of the dosage window 13 of injection device 1, in which a currently selected dose is displayed (e.g. by way of numbers and/or a scale printed on the sleeve 19 of injection device 1, which is visible through the dosage window 13). For instance, the captured image may have a resolution being higher than the resolution of the captured sub-image. The captured image at least shows the numbers printed on the sleeve 19 of injection device 1 which are visible through the dosage window 13.

In a step 904, optical character recognition (OCR) is performed on the image captured in step 903 in order to recognize the numbers printed on the sleeve 19 of injection device 1 and visible through the dosage window 13, because these numbers correspond to the (currently) selected dose. In accord to the recognized numbers, the selected dose is determined, for instance by setting a value representing the selected dose to the recognized numbers.

In a step 905, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

FIG. 5c shows in more detail method steps that are performed when the selected dose is determined based on the use of acoustical and optical sensors. For instance, these steps may be performed in step 502 of FIG. 5a.

In a step 1001, a sound is captured by an acoustical sensor such as acoustical sensor 27 of supplementary device 2.

In a step 1002, it is determined whether or not the captured sound is a click sound. The captured sound may for instance be a click sound that occurs when a dose is dialled by turning dosage knob 12 of injection device 1 and/or when a dose is ejected/injected by pressing injection button 11, and/or when a prime shot is performed. If the captured sound is not a click sound, step 1001 is repeated. Otherwise in a step 1003, an image is captured by an optical sensor such as optical sensor 25 of supplementary device 2. Step 1003 corresponds to step 903 of flowchart 900.

In a step 1004, an OCR is performed on the image captured in step 1003. Step 1004 corresponds to step 904 of flowchart 900.

In a step 1005, it is determined whether or not there is a change in the determined selected dose and, optionally, whether or not the determined selected dose does not equal zero. Step 1005 corresponds to step 905 of flowchart 900.

There might be a slight advantage of the acoustic approach shown in FIG. 5c when it comes to power consumption of the supplementary device, because permanently capturing images or sub-images as shown in FIG. 5b typically is more power consuming than listening to an acoustical sensor such as a microphone.

Figure 6:
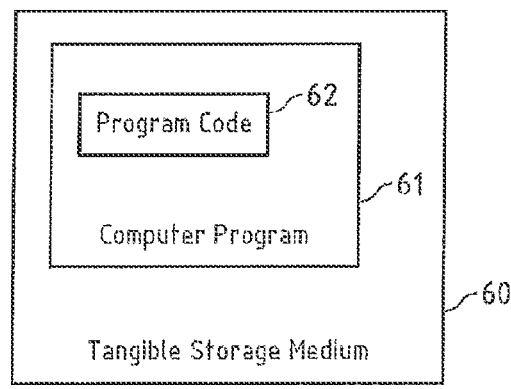
FIG. 6: a schematic illustration of a tangible storage medium 60 according to an embodiment of the present invention.

FIG. 6 is a schematic illustration of a tangible storage medium 60 (a computer program product) that comprises a computer program 61 with program code 62 according to aspects of the present invention. This program code may for instance be executed by processors contained in the supplementary device, for instance processor 24 of supplementary device 2 of FIGS. 2a and 4. For instance, storage medium 60 may represent program memory 240 of supplementary device 2 of FIG. 4. Storage medium 60 may be a fixed memory, or a removable memory, such as for instance a memory stick or card.

Figure 7:
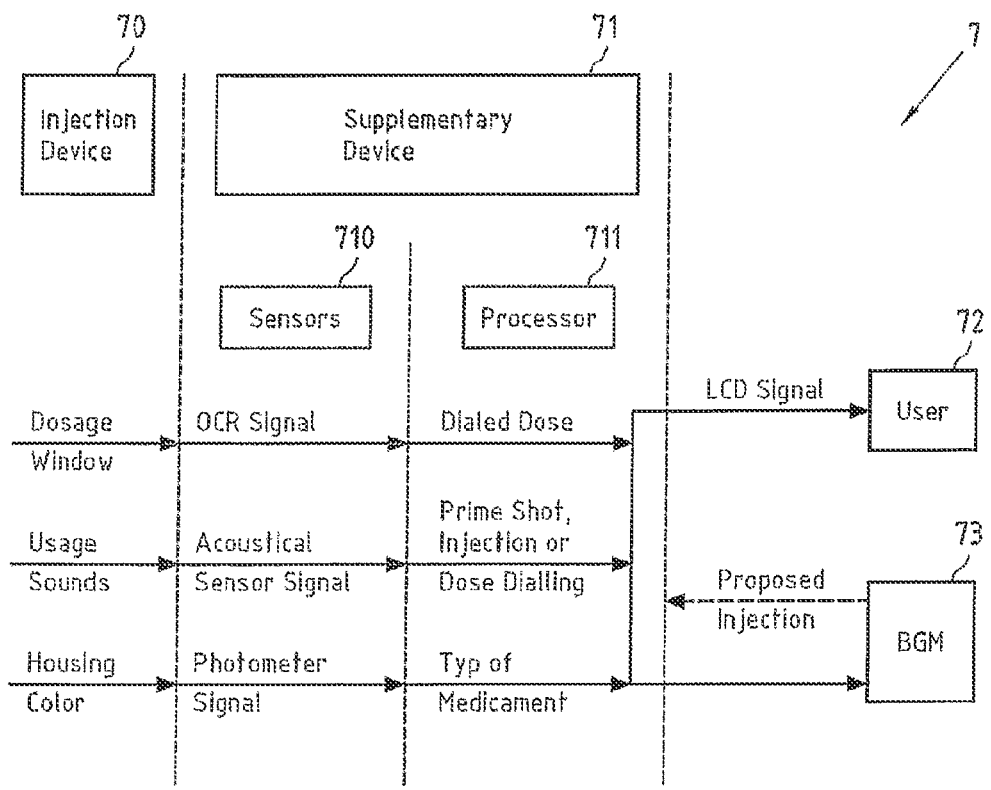
FIG. 7: an information sequence chart that illustrates an information flow between various devices according to embodiments of the invention.
Figure 8:
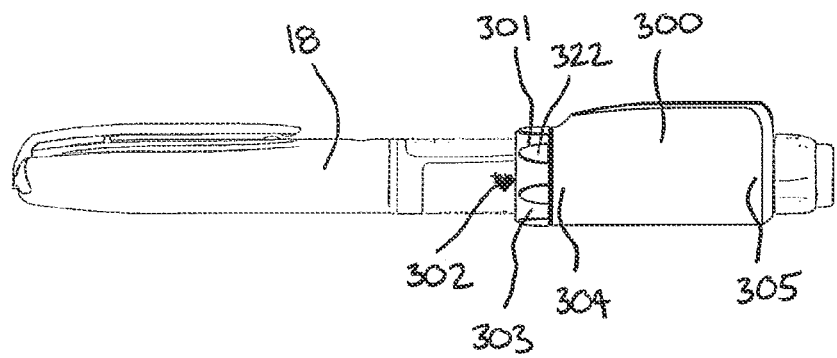
FIG. 8: a side view of the supplementary device shown in FIG. 2b with the injection device of FIG. 1 received through a passage of the supplementary device.

Finally, FIG. 7 is an information sequence chart 7 that illustrates the flow of information between various devices (e.g. the injection device 1 and the supplementary device 2 of FIG. 4 in a scenario as depicted in FIG. 3a or 3b) according to an embodiment of the present invention. A condition and/or use of injection device 70 affects an appearance of its dosage window, sounds generated by injection device 70 and a colour of the housing. This information is transformed by sensors 710 of supplementary device 71 into an OCR signal, an acoustic sensor signal and a photometer signal, respectively, which are in turn transformed into information on the dialled dose, on an injection/dialling operation and on the type of insulin by a processor 711 of supplementary device 71, respectively. This information is then provided by supplementary device 70 to a blood glucose monitoring system 73. Some or all of this information is displayed to a user 72 via the display 21.

As described in detail above, embodiments of the present invention allow connection of a standard injection device, in particular an insulin device, with a blood glucose monitoring system in a useful and productive way.

Embodiments of the present invention introduce a supplementary device to allow for this connection, assuming the blood glucose monitoring system has wireless or other communication capabilities.

The benefits from the connection between the blood glucose monitoring and an insulin injection device are inter alia the reduction of mistakes by the user of the injection device and a reduction of handling steps—no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the supplementary device to the pen by use of the mating unit, as will be described in detail hereinafter. The supplementary device reads out the injected dose. It may also transfer it to a blood glucose monitoring system with insulin titration capabilities. For patients taking multiple insulins, the supplementary device recognizes the device structure to the insulin type and may also transmit this piece of information to the blood glucose monitoring system.

The mating unit for releasably mounting the supplementary device to the injection device in a specific position relative to an outer surface of the injection device will now be described in detail.

The correct alignment of the supplementary device 2 on the injection device 1 ensures that the OCR reader 25 is correctly aligned with the dosage window 13. Correct alignment and location allows correct operation and reliable readings. Ensuring that there can be correct alignment between the supplementary device 2 and the injection device 1 in use allows a simpler design for the OCR reader 25, in particular because it does not need to be designed to be able to accommodate different alignments between the devices 1, 2.

The mating unit comprises the securing unit 301 and the locating unit. The locating unit is configured to locate the body in a specific position relative to the outer surface 106 of the injection device 1. The securing unit 301 is configured to releasably secure the body to the injection device so that the body is retained in the specific position relative to the outer surface 106 of the injection device 1.

Referring to FIGS. 8 to 12, the supplementary device 2 is shown received on the injection device 1. The injection device 1 is received through the passage 302 formed in the body 300. The injection device 1 protrudes from each end of the body 300, with the injection device 1 also protruding through the securing unit 301.

The securing unit 301 comprises the collar 303 and two securing arms; an upper arm 307 and a lower arm 308. The arms 307, 308 act as securing members. The arms 307, 308 extend around an opening 309 to the passage 302 at the front end 304 of the body 300. Therefore, each arm 307, 308 has an arcuate shape. The arms 307, 308 form a circumferentially extending arrangement around the opening 309. Two slots 310 separate the arms 307, 308 from each other. Therefore, side edges 311 of the arms 307, 308 are spaced from each other to allow the arms to deflect relative to each other.

Each arm 307, 308 protrude from a front face 314 of the body 300. The front face 314 is formed at the front end 304 of the body 300. The arms protrude substantially parallel to the longitudinal axis of the injection device receiving passage 302. Each arm has an inner surface 312. The inner surface 312 of each arm acts as a clamping surface. The clamping surface is configured to locate against and mate with the injection device 1. The clamping surface 312 of each arm 307, 308 extends co-planar with the inner surface of the injection device receiving passage 302.

Each arm 307, 308 has an outer surface 313. The outer surface 313 of each arm is arcuate so that the arms together define a cylindrical shape. A circumferentially extending ridge 315 is formed at a free edge 316 of each arm 307, 308. The ridge 315 upstands from the outer surface 313 of each arm. The ridge 315 has a triangular form in cross-section; that is front and rear faces of the ridge 315 are inclined towards each other. Although the ridge 315 on each arm 307, 308 extends along the length of the free edge 316 of each arm 307, 308, it will be understood that each ridge may extend along part of the free edge 316, or be formed in a number of separate portions. The ridge 315 extends parallel to the front face 314 of the body 300.

Each arm 307, 308 is integrally formed with the body 300. Alternatively, the arms are fixedly mounted to the body 300. Each arm 307 is formed from a resilient material so that it is able to flex in a radial direction, as will be explained hereinafter.

An elongate tab 317 is formed on the outer surface 313 of each arm 307, 308. Each elongate tab 317 extends in a circumferential direction along the outer surface 313 of the respective arm. The tab 317 acts as a collar end stop to limit movement of the collar 303 relative to the body 300, as will become apparent hereinafter. The tab 317 is spaced from the front face 314 of the body 300. The tab 317 is also spaced from the ridge 315.

The collar 303 has a toroidal shape. The collar 303 has an outer face 320 and an inner face 321. The outer face 320 has a number of projections 322 formed equidistant around the outer face 320 to enable a user to easily grip the collar 303. Therefore, a user is able to apply a rotational force to rotate the collar 303 relative to the body 300.

The inner face 321 of the collar 303 forms a guide section 323 and a biasing section 324. The biasing section 324 of the collar 303 acts on the arms 307, 308 to urge the arms to deflect in a radial direction. The biasing section 324 has a tapered thread formed thereon which converges towards a front end of the collar, that is the end of the collar disposed distal to the body 300 when the collar 303 is mounted with the body 300. The tapered thread of the biasing section 324 threadingly engages with the ridge 315 on each arm 307, 308.

The biasing section 324 is formed at a front end of the collar 303. The guide section 324 extends from the biasing section 324. A circumferentially extending lip 325 is formed on the inner face 321 of the collar 303. The lip 325 extends inwardly around the rear edge of the inner face 321. The guide section 324 extends between the lip 325 and the biasing section 324.

The collar 303 is rotatably mounted to the arms 307, 308. The collar 303 extends over the arms 307, 308. Therefore, the arms are generally hidden from view by the collar 303 when the collar is mounted to the arms. A rear part of the arms 307, 308 proximate to the front face 314 of the body may be visible to a user when the collar is in its retracted position.

Figure 9:
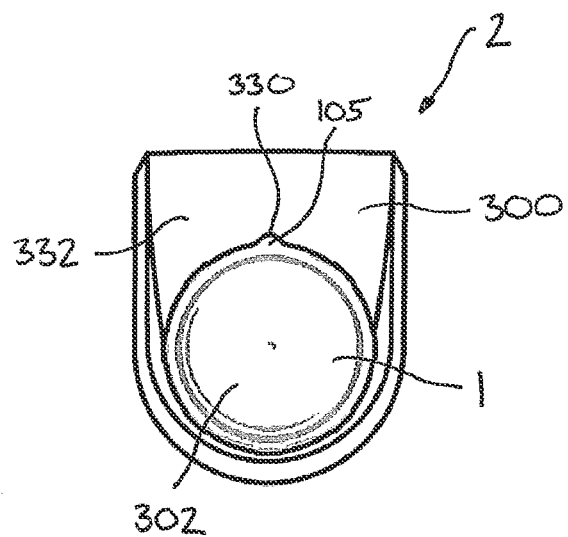
FIG. 9: an end view of the supplementary device shown in FIG. 2b with the injection device of FIG. 1 received through a passage of the supplementary device.

A locating channel 330 is formed in the body 300 (refer to FIG. 9). The locating channel 330 is formed in the inner surface of the passage 302 formed in the body 300. The channel 330 extends from a rear face 332 of the body 300 at the rear end 305 of the body 300. Therefore, the channel 330 forms an opening in the rear face 332 of the body 300 which extends from the rear opening to the passage 302. The locating channel 330 is dimensioned so as to correspond closely to the shape and size of the locating rib 330 that is present on the injection pen 1.

The locating channel 330 has a size and shape that corresponds closely to the size and shape of the locating rib 105. The locating channel 330 is slightly larger than the locating rib so as to ensure that the locating rib can be located within the locating channel 330. When the locating rib 105 is within the locating channel 330, the corresponding sizes ensure that the two features mate together. This assists in ensuring correct positioning of the supplementary device 2 on the injection device 1. The locating channel 330 is open at the rear end of the body 300 and so it will be understood that the rib 105 is able to be slid into the locating channel 330 in a direction of the longitudinal axis of the passage 302.

The locating channel 330 forms part of or the locating unit. The locating unit is configured to locate the body in a specific position relative to the outer surface 106 of the injection device 1. The locating channel 330 forms part of the mating unit configured to embrace the housing 10 of injection device 1 to maintain the supplementary device in a specific position on the injection device 1.

When the securing unit 301 is assembled, the collar 303 is mounted to the arms 307, 308 and extends thereover. The tapered thread of the collar biasing section 324 engages with the ridge 315 on the outer surface 313 of the arms 307, 308. The lip 325 is disposed between the circumferentially extending tab 317 of each arm and the front face 314 of the body 300. Therefore, the collar 303 is able to rotate about the arms 307, 308, thus being rotatable relative to the body 300.

Figure 10:
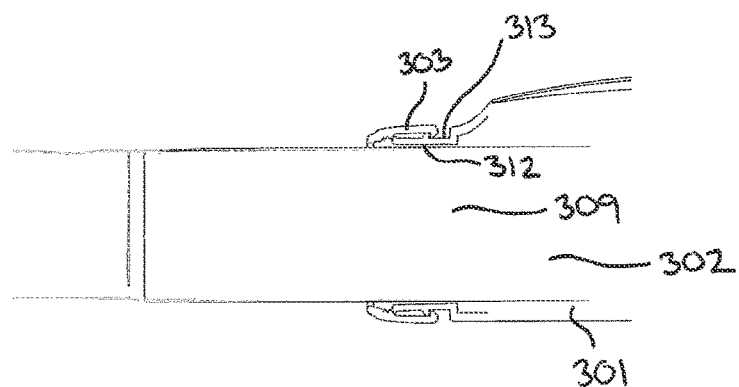
FIG. 10: a cross-sectional side view of the supplementary device shown in FIG. 2b with the injection device of FIG. 1 received through a passage of the supplementary device and a securing unit in a released position.
Figure 11:
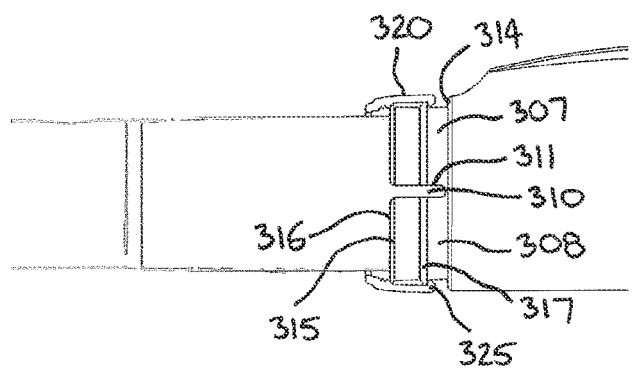
FIG. 11: a partial side view of the supplementary device shown in FIG. 2b with the injection device of FIG. 1 received through a passage of the supplementary device, the securing unit in a released position and a collar of the securing unit shown cut-away.

The securing unit 301 is initially disposed in a retracted position, as shown in FIGS. 10 and 11. In this position, the collar 303 is spaced from the front face of the body. The ridge 315 at the free edge 316 of each arm is disposed at the diverged end of the tapered thread of the biasing section 324. At this position, the arms 307, 308 extend parallel to each other or depend away from each other. The lip 325 of the collar 303 is located against the circumferentially extending tab 317 on the outer surface 313 of each arm. The tab 317 acts as an end stop to limit the movement of the collar 303 along the arms 307, 308. Therefore, rotation of the collar 303 is restricted when the lip 325 abuts against the tab 317 on each arm 307, 308 to prevent the ridge from disengaging from the biasing section and/or the collar from becoming detached from the arms.

To mate the supplementary device 2 on the injection device, the supplementary device 2 is initially located with respect to the injection device. The cap 18 is removed from the injection device 1 and the supplementary device 2 is aligned with the front end of the injection device 1. The body 300 is orientated so that the longitudinal axis of the injection device receiving passage 302 is co-axial with the longitudinal axis of the injection device 1. The supplementary device 2 is received over the injection device 1 so that the injection device is inserted into and received through the passage 302 in the body 300. Therefore, the body 300 acts as a sheath. The body 300 is received over the injection device 1 rear end 305 first. The front section 101 of the injection device 1 is able to easily pass through the passage 302 due to the front section 101 having a smaller diameter than the rear section 102, and therefore the passage 302. The body 300 subsequently slides over the rear section 102. The rear section 102 has a diameter which is slightly smaller than the diameter of the passage 302 so that the injection device 1 is slidable through the passage 302.

As the rear end 305 of the body 300 is slid towards the rear end of the body 300, the locating rib 105 is slid to the rear end 305 of the body 300. A user rotates the body 300 about the longitudinal axis of the injection device so that the locating channel 330 is aligned with the rib 105. The channel 330 is then able to slide over the rib 105 to correctly orientate the body with respect to the injection device 1. The channel 330 is dimensioned so as to correspond closely to the shape and size of the locating rib 105, and so the supplementary device continues to slide over the injection device 1 until the rib 105 is fully received in the channel 330. Therefore, the channel 330 acts as an alignment element for locating the body 300 in a specific position relative to the outer surface 106 of the injection device 1 when the rib 105 is received in the channel 330.

In the event that the user slides the supplementary device 2 onto the injection pen 1 at a location such that the supplementary device 2 is rotated slightly about its longitudinal axis relative to its desired position, the rib 105 will not be received in the channel 330 formed in the body 300. In this case, the supplementary device 2 is prevented from being located fully over the injection device 1 by the rib 105 resting against the rear face 332 of the body 300. A user would know that the supplementary device 2 had not mated correctly with the injection pen 1 because the rib 105 would be clearly visible. They would also notice that the rear end of the supplementary device was spaced from the rear end of the injection device 1. To correctly locate the supplementary device 2 in position with respect to the injection device 1, a user can simply rotate the supplementary device 2 relative to the injection device 1 about the longitudinal axis of the injection device 1. As the supplementary device 2 and the injection device 1 move relative to one another, the locating rib and the channel 330 become aligned with each other. Similarly, if the supplementary device 2 is not correctly aligned on the injection device 1 in a longitudinal direction, the rib 105 will not be fully located in the recess 330.

Once the rib 105 is fully located within the channel 330, the supplementary device 2 is correctly located within the injection device 1. Here, the outermost surface of the display window 13 is aligned with a lowermost surface of the upper part of the supplementary device 2.

Once the body is located in the desired specific position relative to an outer surface of the injection device, the securing unit 301 is then operated to secure the supplementary device 2 on the injection device 1. When the injection device 1 is received through the passage, the injection device is received through the securing unit 301. The injection device 1 is received between the arms 307, 308 such that, when the body 300 is located in the desired specific position, part of the rear section 102 of the injection device is disposed between the arms 307, 308.

Figure 12:
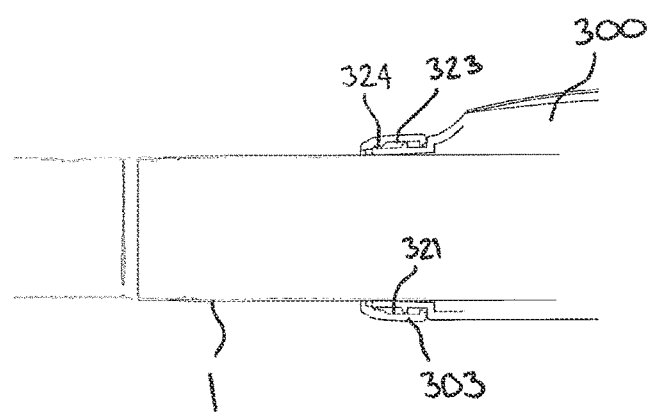
FIG. 12: a cross-sectional side view of the supplementary device shown in FIG. 2b with the injection device of FIG. 1 received through a passage of the supplementary device and the securing unit in a secured position.

A user grasps the body 300 and the collar 303 and then applies a rotational force on the collar 303 to rotate the collar relative to the body 300 in one direction. In FIGS. 8 and 10 to 12, the collar is rotated in a clockwise direction when looking at the injection device from a front end. As the collar 303 is rotated the thread of the collar biasing section 324 which is in engagement with the ridge 315 on the arms 307, 308 urges the collar to move in a longitudinal direction towards the body 300. The thread of the collar biasing section 324 is tapered and so the collar biasing section 324 acts on the free end of each arm to urge the arms to deflect inwardly in a radial direction. The arms 307, 308 are therefore urged to deflect inwardly as the tapered thread, acting on the free edge 316 of each arm, converges. As rotation of the collar 303 continues, the arms 307, 308 continue to be urged towards each other by the biasing section 324. Therefore, the arms 307, 308 are biased towards the outer surface 106 of the injection device 1. The clamping surface 312 of each arm 307, 308 locates against the outer surface 106 of the injection device 1 and are urged thereagainst. Therefore, as the arms 307, 308 are biased towards each other the injection device 1 is clamped between the arms 307, 308. The supplementary device 2 is then securely held in position on the injection device 1 and cannot move relative to the injection device. The securing unit 301 is then in a secured position as shown in FIG. 12.

The thread of the collar biasing section 324 has a fine thread, that is the thread has a small pitch, the collar 303 is not urged to rotate in the opposing direction when the rotational force applied by the user is released. Therefore, the reaction force applied due to the resilience of the arms 307, 308 does not cause the securing unit to move from a secured position to a retracted position.

Rotation of the collar 303 is restricted by the lip 325 of the collar 303 locating against the front face 314 of the body 300. This limits the deflection of the arms 307, 308 by the collar, and so prevents damage to the arms and/or the injection device 1.

It will be appreciated that the above arrangement prevents movement of the injection device 1 relative to the supplementary device 2. In order to remove the supplementary device 2 from the injection device 1, a user exerts a rotational force on the collar 303 to rotate the collar in the opposite direction. The collar 303 then rotates relative to the body 300 and moves in a longitudinal direction away from the body 300. As the ridge 315 at the free edge 316 of each arm 307, 308 moves to the diverged section of the biasing section 324 of the collar 303, the resilience of the arms 307, 308 causes the arms to deflect outwardly in a radial direction away from each other. The arms 307, 308 therefore deflect away from the outer surface of the injection device 1. The clamping surface 312 of each arm is therefore spaced from the outer surface of the injection device 1 such that the injection device is not clamped therebetween. The injection device 1 may then be slid from the supplementary device 2 without being constrained by the securing unit 301.

Figure 13:
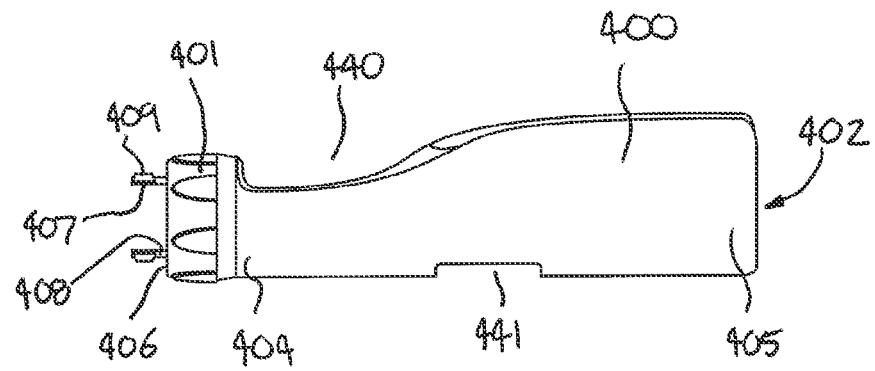
FIG. 13: a side view of another embodiment of the supplementary device with a passage through which the injection device of FIG. 1 is receivable.
Figure 14:
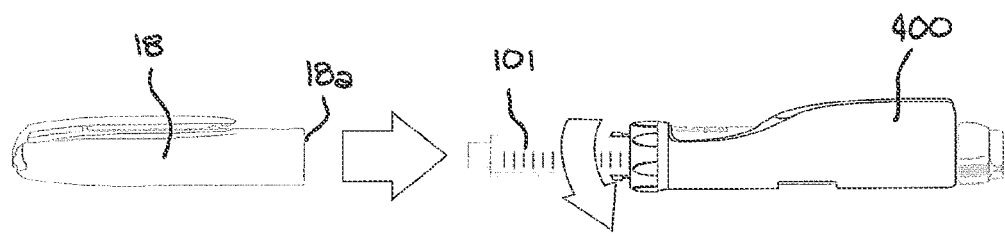
FIG. 14: a side view of the supplementary device shown in FIG. 13 located on the injection device with a cap of the injection device removed.
Figure 15:
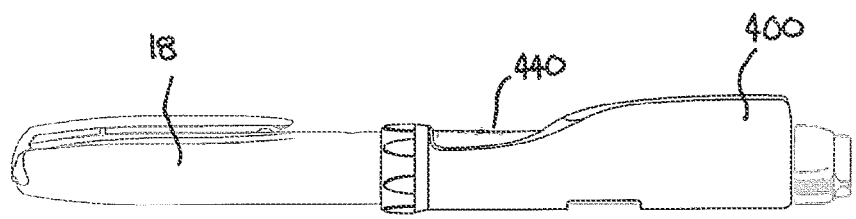
FIG. 15: a side view of the supplementary device shown in FIG. 14 located on the injection device with a cap of the injection device disposed over an end of the injection device and retained in place by the supplementary device.

Referring now to FIGS. 13 to 15, an alternative form of the supplementary device 2 will now be described. Reference numerals are retained from the above-described embodiments. The arrangement and configuration of many of the components and features are generally the same as described above, and so a detailed description will be omitted.

The supplementary unit includes the body 400 and a mating unit. The mating unit comprises the securing unit 401 and the locating unit. The locating unit is configured to locate the body in a specific position relative to the outer surface 106 of the injection device 1. The securing unit 301 is configured to releasably secure the body to the injection device so that the body is retained in the specific position relative to the outer surface 106 of the injection device 1.

In FIG. 13, the supplementary device 2 is shown dismounted from the injection device 1. The supplementary device 2 of this embodiment has a longitudinal length which is longer than that of the supplementary device described above and shown in FIGS. 8 to 12. In this embodiment, the securing unit 401 is arranged to clamp against the front section 101 of the injection device 1. This enables the shoulder 103 between the front and rear sections 101, 102 to be used to aid location of the supplementary device in a specific position on the injection device 1.

A passage 402 extends through the body 400 from a front end 404 to a rear end 405. The passage 402 is configured to slidably receive the injection device therethrough. In the present arrangement, the passage 402 is a cylindrical bore formed through the body 400. A step is formed in the passage 402 formed in the body 400. The step extends circumferentially around the inner surface of the passage 402. The step defines a rear part of the passage 402. The rear part of the passage 402 extends in the rear end 405 of the body 400. The rear part of the passage 402 has a diameter which is slightly greater than the diameter of the rear section 102 of the injection device 1 so that the front and rear sections 101, 102 of the injection device 1 is slidable along the rear part. The step also defines a front part of the passage 402. The rear part of the passage 402 extends from the rear part of the passage 402 and extends in the front end 404 of the body 400. The front part of the passage 402 has a diameter which is slightly greater than the diameter of the front section 101 of the injection device 1. Therefore, the front section 101 is slidable through and along the front part of the passage 402. However, the rear section 102 of the injection device is prevented from sliding along the front part of the passage 402 due to the front part of the passage 402 having a diameter which is slightly less than the diameter of the rear section 102 of the injection device 1. The front section of the passage 402 may be a circumferentially extending flange. Although in the above described embodiment the step is formed in the passage 402 it will be understood that in an alternative embodiment the step is formed between the passage and the securing unit. That is, the diameter of the aperture defined through the securing unit is smaller than the diameter of the passage. In such an arrangement, the diameter of the aperture defined through the securing unit is slightly greater than the diameter of the front section of the injection device, but less than the diameter of the rear section of the injection device. Alternatively, the step may be formed in the securing unit. In this arrangement the clamping surface of each arm may have a step formed in it.

The arrangement of the securing unit is generally the same as the securing unit described in the above embodiment, and so a detailed description will be omitted herein. That is, the arm and collar arrangement of the securing unit is generally the same. The arms act as securing members and extend from the body. Slots separate the arms from each other. However, in this embodiment the slots separating the arms from each other are configured to receive the cap retaining protrusions 104 formed on the outer surface of the front section 101 of the housing 10 of the injection device 1. The slots act as guide slots to aid the location of the supplementary device 2 on the injection device 1. When the supplementary device is slid over the injection device, the cap retaining protrusions 104 upstanding from the front section 101 of the injection device 1 are received in the slots between the arms. Therefore, the slots form part of or act as the locating unit and aid location of the body in a specific position relative to an outer surface of the injection device.

The cap retaining protrusions 104 are disposed proximate to, but spaced from, the shoulder 103 of the injection device. When the cap 18 is received over the front section 101 of the injection device 1 when the supplementary device is omitted, the protrusions 104 locate over one or more retaining elements (not shown) formed on the inner surface of the cap 18 to retain the cap 18 in position over the front section 101. However, it will be understood that in the present embodiment the supplementary device extends partially along the front section of the supplementary device. Therefore, it is not possible for the cap 18 to be retained by the retaining elements.

In the present embodiment, the supplementary device further comprises two auxiliary cap retaining members 407 extending from a front side 406 of the securing unit 401.

The auxiliary cap retaining members 407 each comprise a finger 408 and a cap retaining protrusion 409. The fingers 408 of the cap retaining members 407 are spaced from each other to receive the front section of the injection device therethrough. That is, when the fingers 408 are spaced diametrically opposite each other, the distance between the inner surface of the fingers 408 corresponds to the diameter of the front section 101. The fingers 408 extend from the front side 406 of the securing unit 401. In the present embodiment the fingers extend from the free edge of each securing arm of the securing unit, and extend past the front edge of the collar. Alternatively, the fingers 408 extend from the front edge of the collar.

The thickness of the fingers 408 of the cap retaining members 407 is less than the height of the retaining elements between the injection device outer surface and the distal edge. The cap retaining elements 409 have a height corresponding to the height of the retaining protrusions. That is, the distance between the inner surface of the fingers 408 and the free edge of the cap retaining elements 409 is the same as the height of the retaining protrusions between the injection device outer surface and the distal free edge of the cap retaining protrusions 104. Therefore, the cap 18 will engage with the cap retaining elements 409 when the fingers are disposed against the outer surface of the front section 101 of the injection device 1. Similarly, the distance between the cap retaining elements 409 and the front edge 406 of the securing unit 401 is equal to the distance between the cap retaining protrusions on the injection device and the shoulder of the injection device 1. Therefore, the cap rim 18a will locate against the front edge 406 of the securing unit 401 when the cap is engaged with the cap retaining elements 409.

To mate the supplementary device 2 on the injection device, the supplementary device 2 is initially located with respect to the injection device. The cap 18 is removed from the injection device 1 and the supplementary device 2 is aligned with the front end of the injection device 1. The body 400 is orientated so that the longitudinal axis of the injection device receiving passage 402 is co-axial with the longitudinal axis of the injection device 1. The supplementary device 2 is received over the injection device 1 so that the injection device is inserted into and received through the passage 402 in the body 400. Therefore, the body 400 acts as a sheath. The body 400 is received over the injection device 1, with the rear end 405 being received over first. The front section 101 of the injection device 1 is able to pass through the front part of the passage 402 due to the front section 101 having a smaller diameter front part of passage 402. The rear section 102 of the injection device 1 is subsequently slid into the passage 102. The rear section 102 is able to slide into the rear part of the passage 402, but is prevented from sliding into the front part due to the rear section 102 of the injection device 1 having a diameter which is greater than the diameter of the front part of the passage 402. Therefore, the shoulder of the injection device abuts against the step. Therefore, the step mates with the shoulder and acts as a locating element. At the same point, the locating rib 105 is received in the locating channel formed in the body. The supplementary device is then correctly orientated with respect to the injection device 1. The step is formed along the supplementary device so that the body 400 is located in a specific position relative to the outer surface 106 of the injection device 1 in a longitudinal direction when the shoulder is received against the step.

In the event that the user does not locate the shoulder against the step, the rib 105 will not be received in the channel formed in the body. A user would then know that the supplementary device 2 had not mated correctly with the injection pen 1 because the rib 105 would be clearly visible.

Once the supplementary device 2 is correctly located within the injection device 1, the user engages the securing unit 401 as described in the above embodiment. Therefore, a detailed description will be omitted.

The cap retaining elements are then received against and extend along the outer surface of the front section 101 of the injection device 1. A user is then able to locate the cap 18 over the front section 101 and engage the cap with the cap retaining elements 407.

As shown in FIGS. 13 to 15, an opening 440 is formed in the body 400 of the supplementary device 2 to allow a user to view information on the injection device 1 that would otherwise be hidden by the body 400. A secondary opening 441 is formed on the opposing side of the body 400. The openings allow the label (not shown) provided on the housing 10 to be visible to a user. Therefore a user is able to view the label to view information about the medicament included within the injection device, including information identifying the medicament without removing the supplementary device 2.

Although in the above embodiment the tapered thread is formed on the collar and engages with a part-circumferentially extending ridge on each arm, it will be understood that the tapered thread may be formed on the outer surface of each arm and the corresponding ridge formed on the inner face of the collar. Alternatively, a tapered thread may be formed on each of the collar and each arm.

In an alternative arrangement the collar and each arm are threadingly engaged by a parallel thread arrangement, and part of the inner face of the collar has a conical biasing face which acts on each arm as the collar is rotated about the body. Similarly, a conical or diverging face may be formed on the outer surface of each arm against which the inner face of the collar acts.

Although two engaging arms are shown in the Figures and described above, it will be appreciated that the securing unit 301 may include a different number of engaging arms. For example, in an alternative arrangement the securing unit may have three or four engaging arms.

Although the securing unit and locating unit are separate in the above described embodiments, it will be appreciated that the two units may be integral with each other. For example, the rear end of the arms may have a step formed in them. Referring now to FIGS. 16 to 19, an alternative form of the supplementary device 2 will now be described. Reference numerals are retained from the above-described embodiments. The arrangement and configuration of many of the components and features are generally the same as described above, and so a detailed description will be omitted.

The supplementary unit includes a body 500 and a mating unit. The mating unit comprises a securing unit 501 and a locating unit. The locating unit is configured to locate the body in a specific position relative to the outer surface 106 of the injection device 1. The securing unit 501 is configured to releasably secure the body to the injection device so that the body is retained in the specific position relative to the outer surface 106 of the injection device 1. A passage extends through the body 500 from a front end to a rear end. The passage is configured to slidably receive the injection device therethrough. In the present arrangement, the passage is a cylindrical bore formed through the body.

The locating unit is generally the same as for the above described embodiments. For example, the body may be aligned by the locating channel receiving the locating rib therein, and/or by a step locating against the shoulder of the injection device. Therefore, a further description will be omitted herein.

However, in the present embodiment the supplementary device is secured to the injection device by protuberances 502 which locate in the indents 108 formed in the outer surface of the injection device 1. The body 500 has an outer shell 503 and an inner shell 504. The outer shell 503 is omitted in FIGS. 18 and 19. The passage for receiving the injection device is formed by the inner shell 504. An inner surface of the inner shell forming the passage acts as a clamping surface against which the injection device is located to clamp the injection device in a desired position relative to the supplementary device.

Figure 18:
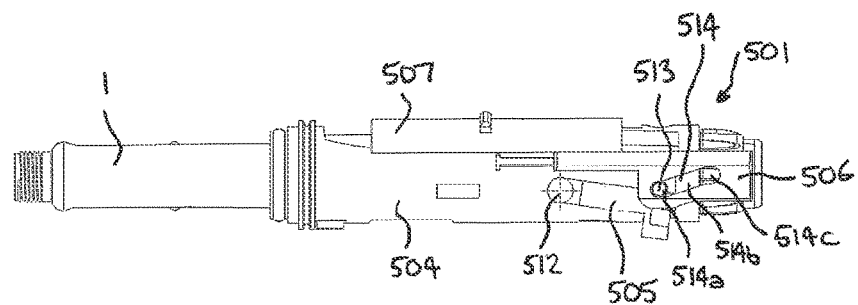
FIG. 18: a side view of the supplementary device shown in FIG. 16 located on the injection device with an outer shell of the body removed.
Figure 19:
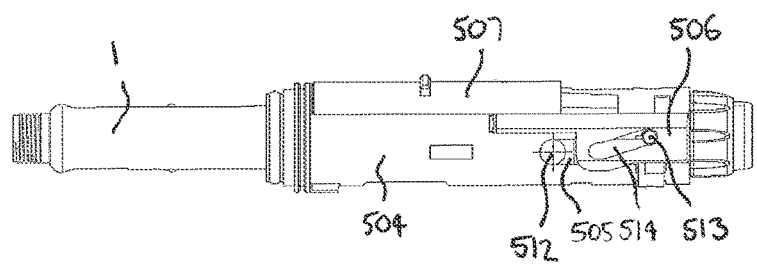
FIG. 19: a side view of the supplementary device shown in FIG. 16 located on the injection device with an outer shell of the body removed.

In FIG. 18, the supplementary device 2 is shown mounted to the injection device 1. The securing unit 501 is shown in a retracted position, in which the protuberances 502 are pivoted away from the longitudinal axis of the injection device receiving passage formed through the body 500 not engaged in the indents 108. The securing unit 501 comprises an actuating member 505, two guide members 506 disposed on opposite sides of the inner shell 504, and an operating button 507.

Figures 16, 17:
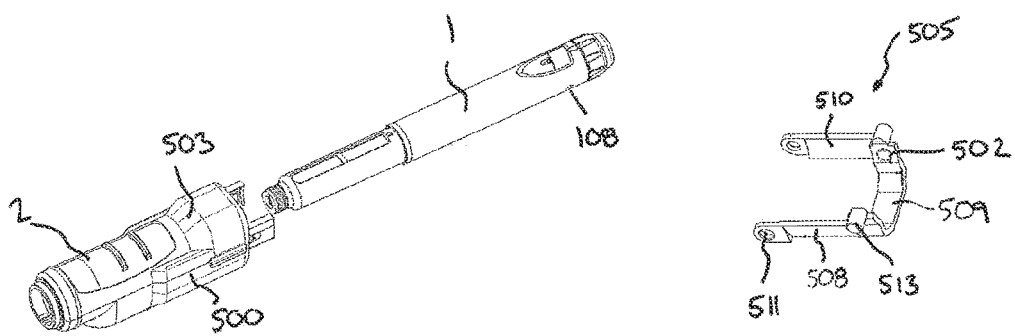
FIG. 16: a perspective view of another embodiment of the supplementary device with the injection device of FIG. 1 received through a passage of the supplementary device.
FIG. 17: a perspective view of an actuating member of the supplementary device.

The actuating member 505 is shown in FIG. 17 detached from the body 500. The actuating member 505 has a U-shaped frame 508. The U-shaped frame 508 has a base 509 and left and right pivot legs 510 extending from the base 509. The base 509 itself has a U-shaped arrangement so that it can extend around a lower side of the inner shell 504 of the body 500 and connects the two pivot legs 510 to each other. Pivot holes 511 are formed at the distal end of each pivot leg 510 through which pivot pins 512 extend to pivotally mount the actuating member 505 to the inner shell 504. The pivot axis of the actuating member 505 extends perpendicular to the longitudinal axis of the injection device receiving passage formed through the body 500, and thus perpendicular to the longitudinal axis of the injection device 1 when received through the supplementary device 2. The actuating member 505 is therefore free to pivot towards and away from the inner shell of the body 500.

Two protuberances 502 are formed on the actuating member 505. One protuberance 502 is formed on an inner face of each of the pivot legs 510. The protuberances 502 are disposed at an opposing end of the pivot legs 510 to the pivot holes 511. Each protuberance 502 acts as an engaging element to engage in the indents 108 formed in the outer surface of the rear section 102 of the injection device 1. Therefore, it will be understood that the protuberances act as clamping surfaces to mate with the injection device. The protuberance 502 on the left pivot leg is configured to be received in the left indent 108. The protuberance 502 on the right pivot leg is configured to be received in the left indent 108. The protuberances 502 are shaped to correspond closely to the shapes of the indents 108 respectively. In this way, the protuberances 502 fit snugly within the corresponding indents 108 respectively when the supplementary device 2 is correctly positioned on the injection device 1 and the actuating member 505 is moved into its secured position. The external dimensions of the protuberances 502 are slightly smaller than the internal dimensions of the indents 108 so as to ensure that the protuberances 502 fit within their respective indent. An opening (not shown) is formed on each side and along the underside of the inner shell 504 into which the actuating member 505 is receivable so that the protuberances 502 are able to engage with the injection device 1.

A guide rod 513 extends outwardly from an opposing side of each pivot leg 510 to the protuberances 502. The guide rods 513 are cylindrical. Each guide rod 513 is arranged to be received in a guide slot 514 formed in each guide member 506. The guide members are disposed on opposing sides of the inner frame of the body 500. The guide members are slidably mounted to the inner frame 504 of the body 500. The guide members 506 are mounted to the body 500 to slide along a path defined to extend parallel to the longitudinal axis of the injection device receiving passage formed through the body 500, and thus parallel to the longitudinal axis of the injection device 1 when the device is received through the supplementary device 2. Each guide member 506 has one guide slot formed therein. The width of the guide slot corresponds to the diameter of the guide rod 513 received therein so that the guide rod 513 is slidable therealong.

Each guide slot 514 has a first section 514a, a second section 514b and a third section 514c. The first and third sections 513a, 513c are formed in the guide member 506 to extend parallel to the path of the guide member 506 relative to the body 500. The second section 513b extends at an angle to the path of the guide member 506 relative to the body 500. The guide slots 514 act as a cam.

The operating button 507 is fixedly mounted to the guide members 506 and extends over an upper side of the inner shell 504. The operating button 507 extends into an aperture formed in the outer shell 503 of the body 500 so that it is operable by a user. The length of the aperture is greater than the length of the button so that the operating button is slidable therein.

When the securing unit 501 is assembled, the guide members 506 and operating button 507 are slidably mounted to the body to slide in a longitudinal direction. The actuating member 505 is pivotably mounted to the body 500, with the guide rods 513 being received in the corresponding guide slots 514. The securing unit 501 is initially in a retracted position, with the protuberances 502 pivoted away from their engaging position. The injection device 1 is then received in the body 500, and the locating unit locates the body in a specific position relative to an outer surface of the injection device. The locating unit is generally the same as recited in the above-described embodiments and so a detailed description will be omitted herein.

When the injection device is received through and correctly aligned with the supplementary device 2, the indents 108 are aligned with the opening formed in the inner shell 504. The guide rods 513 are received in the first section 514a of the guide slots 514. The second section 514b extends at an angle to the first section 514a, and so the guide rod is not inclined to slide into the second section 514b. A user grasping the body 500 of the supplementary device 2 is able to urge the operating button 507 in an axial direction. As the operating button 507 is urged to slide relative to the body 500, the guide members 506 are also urged to slide as they are fixedly mounted to the operating button 507. The operating button 507 and guide members 506 may be integrally formed. When the guide members 506 slide along their path, the sides of the guide slots 514 act on the guide rods 513 received therein. The guide rods 513 slide from the first section 514a into the second section 514b of the guide slot 514. When the guide rods 513 slide in the second section of the guide slot 514 they are biased to move in a direction perpendicular to the path of the guide members 506 due to the inclined arrangement of the second section 514b. The guide rods 513 are on the actuating member 505 and so the actuating member 505 is also urged to move, and so pivot about its pivot axis.

When the actuating member 505 pivots about its pivot axis, the protuberances 502 at the free end of each pivot leg 510 of the actuating member 505 are biased towards the longitudinal axis of the body 500, and therefore indents 108 formed in the outer surface of the injection device 1. The arrangement of the actuating member 505 is such that the distance between the innermost surfaces of the protuberances 322 is slightly less than the distance between the bottoms of the indents 107. The actuating member 505 is resilient such that the effect of the bias of each leg 510 is to resist movement of the protuberances 502 away from one another. As the actuating member 505 is further pivoted about its pivot axis the protuberances contact the outer surface of the injection device 1. The protuberances act as clamping surfaces and urge the injection device towards the opposing surface of the passage in which the injection device is received. When the surface of the passage is in contact with the injection device the surface of the passage acts as a clamping surface. Further urging causes the protuberances to be biased away from each other until they are aligned with the indents 108. At this point, the resilience of the actuating member 505 causes the protuberances to engage in the indents 108. The securing unit 501 is then in its secured position. It will be understood that the injection device is clamped between the clamping surfaces formed by the protuberances and the surface of the passage. It will also be understood that the base 509 of the actuating member 505 may also act as a locating surface and that the injection device may be clamped between the locating surface of the base and the opposing locating surface of the passage. It will be understood that in an alternative arrangement that the protuberances may be omitted and that the injection device may be clamped between the locating surface of the base and the opposing locating surface of the passage.

To disengage the protuberances 502 from the indents 102, the user urges the operating button to slide in the opposing direction. This causes the guide members 506 to slide in the opposing direction. Therefore, the actuating member 505 is urged to pivot in the opposite direction. The protuberances 502 are urged out of the indents 108, and so disengage from the indents 108 when a sufficient force is applied by a user. The protuberances 502 are then pivoted about the pivot axis of the actuating member 505 to retract them away from the injection device 1 until the securing unit 501 is in its retracted position. The indents 108 have chamfered sides to allow the protuberances 502 to slide out of the indents 108 when a sufficient force is applied.

The injection device 1 may then be slid from the supplementary device.

Although in the above arrangement the actuating member 505 and protuberances are pivoted by a guide member 506 acting in a longitudinal direction, it will be understood that alternative guides may be used. For example, a lever may be used to act on the actuating member 505.

Figure 20:
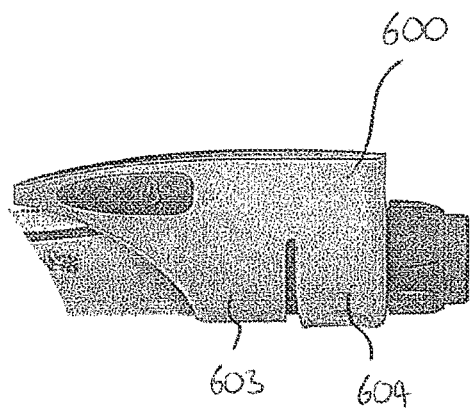
FIG. 20: a side view of another embodiment of the supplementary device with the injection device of FIG. 1 received through a passage of the supplementary device.
Figure 21:
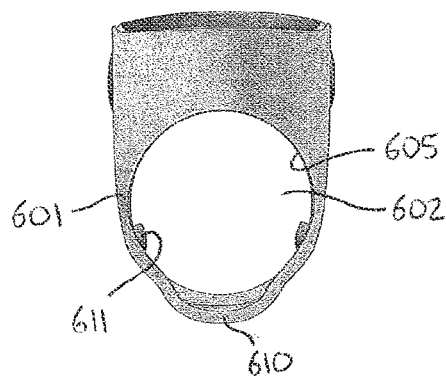
FIG. 21: a rear view of the supplementary device shown in FIG. 2o with a securing unit in a secured condition.
Figure 22:
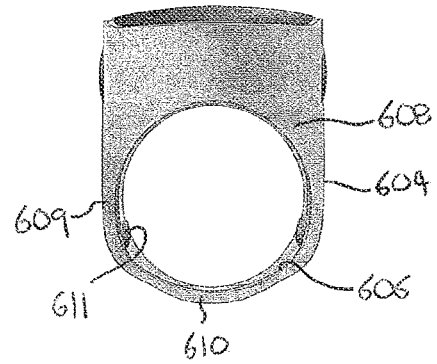
FIG. 22: a rear view of the supplementary device shown in FIG. 2o with a securing unit in a released condition.

Referring now to FIGS. 20 to 22, an alternative form of the supplementary device 2 will now be described. Reference numerals are retained from the above-described embodiments. The arrangement and configuration of many of the components and features are generally the same as described above, and so a detailed description will be omitted.

The supplementary unit includes a body 600 and a mating unit. The mating unit acts as a securing unit 601. The securing unit 601 is configured to releasably secure the body to the injection device so that the body is retained in a specific position relative to the outer surface 106 of the injection device 1. The securing unit 601 also acts as a locating unit configured to locate the body in the specific position relative to the outer surface 106 of the injection device 1.

Alternatively, the locating unit is separate to the securing unit 601, and takes generally the same form as described in the above embodiments. For example, the body may be aligned by the rib receiving channel (not shown) receiving the locating rib therein, and/or by a step locating against the shoulder of the injection device. Therefore, a further description will be omitted herein.

A passage 602 extends through the body 600 from a front end to a rear end. The passage is configured to slidably receive the injection device therethrough. In the present arrangement, the passage is a cylindrical bore formed through the body. The passage 602 includes a sleeve section 603 at a front end, and a deformable collar section 604 at a rear end of the body 600. The rib receiving channel (not shown) is formed in the inner surface 605 of the passage 602 to receive the rib 105 to allow the body 600 to slide axially along the injection device 1.

The inner surface of the sleeve section 603 of the passage 602 has a diameter which is slightly greater than the diameter of the rear section 102 of the injection device 1 so that the injection device 1 is slidable through the sleeve section 603. However, the injection device 1 is prevented from moving in a radial direction relative to the supplementary device when the injection device is received through the sleeve section 603.

The inner surface 606 of the deformable collar section 604 of the passage 602 has a diameter which conforms to the diameter of the rear section 102 of the injection device 1, when the collar section 604 is in its undeformed condition. The deformable collar section 604 has an upper part 607 and a lower part 608. The upper part 607 is substantially rigid and is not able to deform. The lower part 608 of the deformable collar section 604 is formed to be resilient and to be able to deform in response to an urging force applied to it. That is, the thickness of the lower part 608 of the collar section 604 between an outer surface 609 and the inner surface 605 is minimised to allow the lower part 608 to deform. The lower part 608 is resilient, so that the collar section 604 can be manipulated between an initial undeformed condition and a deformed condition.

The inner surface 606 of the deformable collar section 604 is generally cylindrical, however the lower part 608 has an outwardly extending arched portion 610 (refer to FIG. 21). The arched portion 610 extends away from the longitudinal axis of the passage 602.

Protuberances 611 are formed on the inner surface 606 of the deformable collar section 604. The deformable collar section 604 has one left protuberance and one right protuberance. Each protuberance 611 is formed on the lower part 608 of the deformable collar section 604. The protuberances 611 are disposed on each side of the outwardly extending arched portion 610.

The supplementary device 2 is secured to the injection device 1 by the protuberances 611 which locate in the indents 108 formed in the outer surface of the injection device 1. Each protuberance 611 acts as an engaging element to engage in the indents 108 formed in the outer surface of the rear section 102 of the injection device 1. Therefore, it will be understood that the protuberances act as clamping surfaces to mate with the injection device. The left protuberance 611 is configured to be received in the left indent 108. The right protuberance 611 is configured to be received in the left indent 108. The protuberances 611 are shaped to correspond closely to the shapes of the indents 108 respectively. In this way, the protuberances 611 fit snugly within the corresponding indents 108 respectively when the supplementary device 2 is correctly positioned on the injection device 1. The external dimensions of the protuberances 611 are slightly smaller than the internal dimensions of the indents 108 so as to ensure that the protuberances 611 fit within their respective indent.

In FIG. 20, the supplementary device 2 is shown mounted to the injection device 1. The securing unit 601 is shown in a secured position, in which the protuberances 611 are engaged in the indents 108. The securing unit 601 is in its secured position when the deformable collar section 604 is in its undeformed condition (as shown in FIG. 21).

To mate the supplementary device 2 with the injection device 1, a user slides the rear section 102 of the injection device through the passage 602 of the supplementary device 2. That is, the sleeve section 603 is received over the rear end of the injection device 1 and is slid therealong in an axial direction. The deformable collar section 604 is then aligned with the rear end of the injection device 1. The deformable collar section 604 is initially in its undeformed condition. To allow the deformable collar section 604 to slide over the rear section 102 of the injection device, the user grasps the body 600 of the supplementary device 2, for example between their thumb and forefinger.

The user then applies a compressive force to the collar section 604 to urge the collar section 604 to flex and therefore deform. This is achieved by the user locating one of their thumb or forefinger against the outer surface of the arched portion 610 and the other of the thumb and forefinger against an opposing side of the outer surface of the body 600. When the user urges the deformable collar section to deform by applying a radial force to the arched portion 610, the arched section distends inwardly and uncurls or straightens out. This causes the lower part 608 of the deformable collar section 604 on each side of the arched section 610 to deflect outwardly. The inner surface 606 at these portions of the deformable collar section 604 therefore deform outwardly, and the protuberances 611 also distend outwardly. The protuberances 611 are biased away from each other. Therefore, the securing unit 601 is in a retracted position, in which the protuberances 611 are disengaged from the indents 108. The securing unit 601 is in its retracted position when the deformable collar section 604 is in its deformed condition (as shown in FIG. 22). The collar section 604 may then be slid over the rear section 102 of the injection device 1.

When the injection device is received through and correctly aligned with the supplementary device 2, the indents 108 are aligned with the indents 108. The user then releases the compressive force applied on the deformable collar section 604. The resilience of the deformable collar section 604 urges it to return to its undeformed condition. As the deformable collar section 604 returns to its undeformed condition, it moves from its retracted position (as shown in FIG. 22) to its secured position (as shown in FIG. 21). At this point, the resilience of the deformable collar section 604 causes the protuberances 611 to be biased inwardly, and so the protuberances engage in the indents 108. The securing unit 501 is then in its secured position. In the event that the protuberances 611 are not correctly aligned with the indents 108, the user moves the supplementary device relative to the injection device until they are aligned. At this point, the resilience of the deformable collar section 604 causes the protuberances 611 to engage in the indents 108, and the user is provided with a haptic feedback to indicate that the supplementary device 2 and injection device 1 are correctly mated with each other.

To disengage the protuberances 611 from the indents 102, the user reapplies the compressive force to the deformable collar section 604 causing the deformable collar section 604 to deform. The protuberances 611 are urged out of the indents 108, and so disengage from the indents 108 when a sufficient force is applied by a user.

The injection device 1 may then be slid from the supplementary device 2.

Referring now to FIGS. 23 to 31, an alternative form of the supplementary device 2 will now be described. Reference numerals are retained from the above-described embodiments. The arrangement and configuration of many of the components and features are generally the same as described above, and so a detailed description will be omitted.

The supplementary unit includes the body 700 and a mating unit. The mating unit comprises the securing unit 701 and the locating unit. The locating unit is configured to locate the body in a specific position relative to the outer surface 106 of the injection device 1. The securing unit 701 is configured to releasably secure the body to the injection device so that the body is retained in the specific position relative to the outer surface 106 of the injection device 1.

Figure 23:
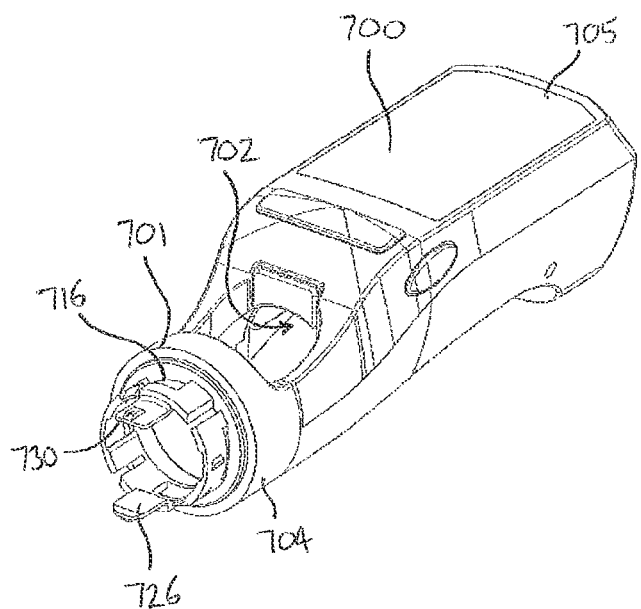
FIG. 23: a perspective view of another embodiment of the supplementary device with a passage through which the injection device of FIG. 1 is receivable and with a collar of the device omitted.
Figure 24:
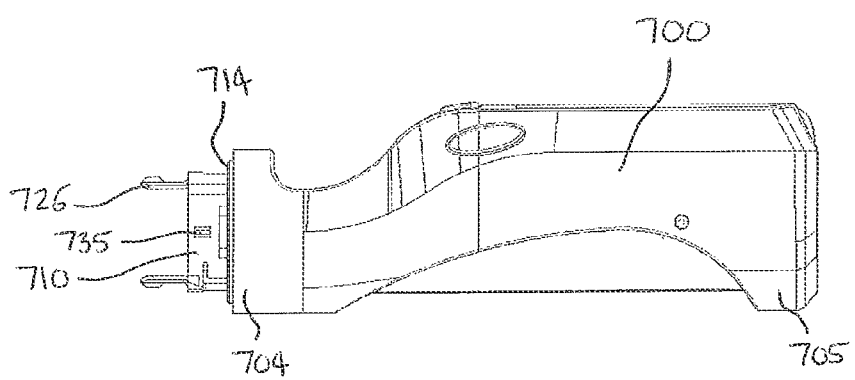
FIG. 24: a side view of the supplementary device shown in FIG. 23 with the collar of the device omitted.
Figure 25:
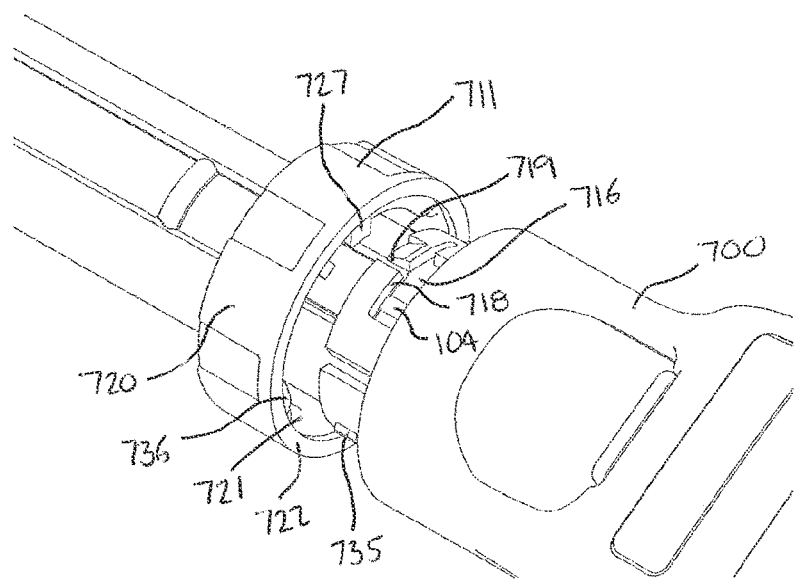
FIG. 25: a perspective view of the supplementary device shown in FIG. 23 with the injection device of FIG. 1 received through the passage and with the collar of the device shown in an exploded position.

In FIG. 23, the supplementary device 2 is shown dismounted from the injection device 1. The supplementary device 2 of this embodiment has a longitudinal length which is longer than that of the supplementary device described above and shown in FIGS. 8 to 12. In this embodiment, the securing unit 701 is arranged to clamp against the front section 101 of the injection device 1. This enables the shoulder 103 between the front and rear sections 101, 102 to be used to aid location of the supplementary device in a specific position on the injection device 1, and also to secure the supplementary device in said specific position.

A passage 702 extends through the body 700 from a front end 704 to a rear end 705. The passage 702 is configured to slidably receive the injection device therethrough. In the present arrangement, the passage 702 is a cylindrical bore formed through the body 700. A step 703 is formed in the passage 702 formed in the body 700 (refer to FIG. 30). The step 703 extends circumferentially around the inner surface of the passage 702. The step 703 is configured to abut against the shoulder 103 of the injection device 1. The step defines a rear part 707 of the passage 702 (refer to FIG. 30). The rear part 707 of the passage 702 extends in the rear end 705 of the body 700. The rear part 707 of the passage 702 has a diameter which is slightly greater than the diameter of the rear section 102 of the injection device 1 so that the front and rear sections 101, 102 of the injection device 1 are slidable along the rear part 707 of the passage 702. The step 703 also defines a front part 706 of the passage 702 (refer to FIG. 30). The front part 706 of the passage 702 extends from the rear part of the passage 702 and extends in the front end 704 of the body 700. The front part 706 of the passage 702 has a diameter which is slightly greater than the diameter of the front section 101 of the injection device 1. Therefore, the front section 101 is slidable through and along the front part 706 of the passage 402. However, the rear section 102 of the injection device is prevented from sliding along the front part 706 of the passage 702 due to the front part 706 of the passage 702 having a diameter which is less than the diameter of the rear section 102 of the injection device 1. The front part 706 of the passage 702 may be a circumferentially extending flange.

Two cut-outs 708 are formed in the surface of the front part 706 of the passage 702. Each cut-out 708 extends in an axial direction, that is parallel to, but spaced from, the longitudinal axis of the passage 702. Each cut-out 708 extends between the face of the step 703 and a front face 714 of the body 700. Each cut-out 708 is dimensioned to allow one of the two cap retaining protrusions 104 formed on the outer surface of the front section 101 of the housing 10 of the injection device 1 to pass therethrough. The cap retaining protrusions 104 are disposed proximate to, but spaced from, the shoulder 103. The two protrusions are disposed diametrically opposite each other and so the cut-outs 708 are formed diametrically opposite each other.

In the present embodiment, the front end 704 is formed from two parts, an inner part 704a and an outer part 704b to aid manufacture of the supplementary device 2. The inner and outer parts 704a, 704b are fixedly mounted to each other. It will also be understood that the inner and outer parts 704a, 704b may be integrally formed.

The securing unit 701 comprises an inner collar 710 and an outer collar 711. The inner collar 710 extends around an opening 712 to the passage 302 at the front end 304 of the body 300. The inner collar 710 extends from the front face 714 of the body 700. The inner collar 710 is integrally formed with the front end of the body 700. An inner face 713 of the inner collar 711 extends co-planar with the inner surface of the front part of the passage 702. The inner collar 710 has an outer face 715. Therefore, each the inner collar 710 has a circumferential arrangement. Two slots 716 are formed in the inner collar 710. Each slot 716 extends in a circumferential direction around the inner collar 711. Each slot 716 is arcuate. The two slots 716 are formed diametrically opposite each other in the inner collar 710. Each slot 716 extends between the inner and outer faces 713, 715 of the inner collar 711 to communicate therebetween. Each slot 716 is elongate in a circumferential direction. A rear edge 717 of each slot is formed by the front face 714 of the body. The width of each slot 716 in an axial direction of the passage 702 between the rear edge 717 and a front edge 718 is greater than the length of each cap retaining protrusion 104 in an axial direction of the injection device 1. The rear and front edges 717, 718 extend parallel to each other.

Figure 26:
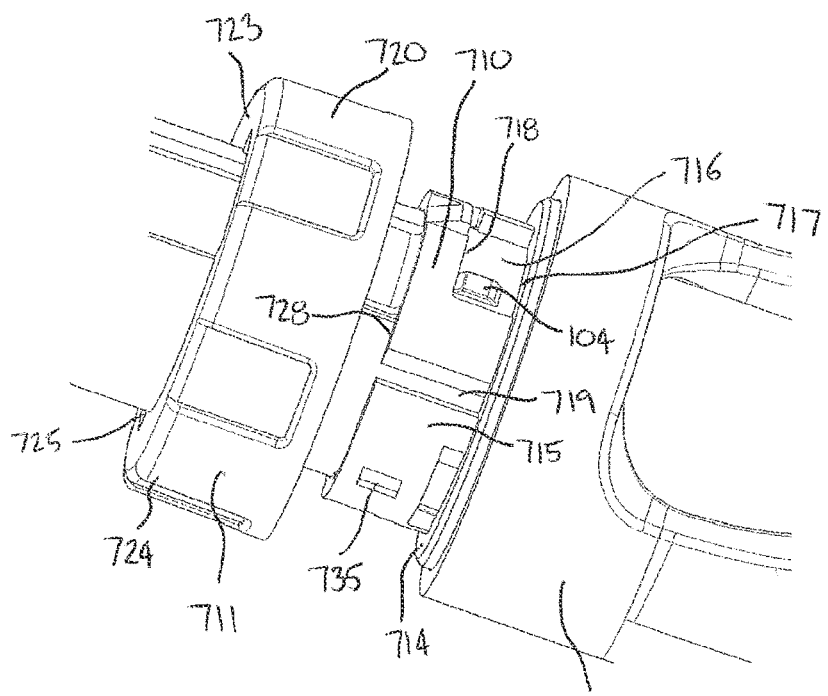
FIG. 26: another perspective view of the supplementary device shown in FIG. 23 with the injection device of FIG. 1 received through the passage and with the collar of the device shown in an exploded position.
Figure 27:
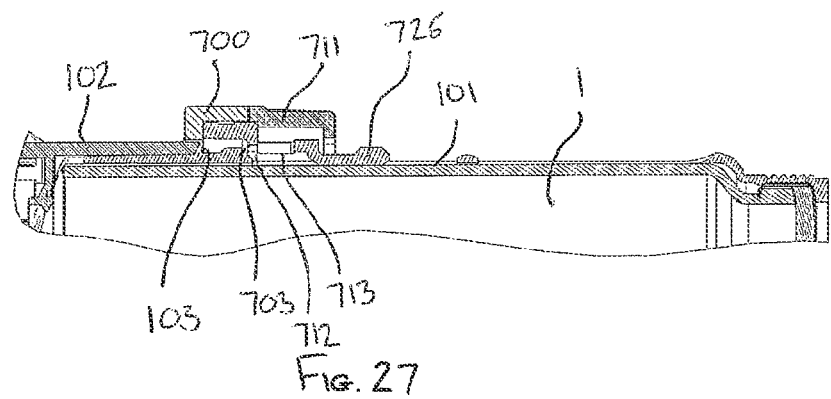
FIG. 27: a cross-sectional side view of the supplementary device shown in FIG. 23 with the injection device of FIG. 1 received through the passage prior to the supplementary device locating against the step of the injection device.

Each slot 716 is aligned with an opening in the front face 714 of the body 700 to one of the cut-outs 708 (opening omitted in FIGS. 23 and 26). Therefore, when the cap retaining protrusions 104 pass through the cut-outs 708, they are received in a corresponding slot 716. Breaks 719 are formed in the inner collar 710 to aid assembly of the outer collar 711 to the inner collar 710.

The outer collar 711 has a toroidal shape. The outer collar 711 is shown in an exploded position in FIGS. 25 and 26. The outer collar 711 has an outer face 720 and an inner face 721. The outer face 720 has outer indentations formed on it to enable a user to easily grip the outer collar 711. Therefore, a user is able to apply a rotational force to rotate the outer collar 711 relative to the body 700. The outer collar 711 extends over the inner collar 710 and is rotatably mounted thereto. The outer collar 711 is separate to the inner collar 710. The outer collar 711 is rotatable around the inner collar 710 about the longitudinal axis of the passage 702 formed in the body 700.

The outer face 720 of the outer collar 711 is cylindrical and has an outer diameter which generally corresponds to the outer surface of the body 700. The inner face 721 of the outer collar 711 is cylindrical. The inner face 721 has a diameter which is slightly greater than the diameter of the outer face 715 of the inner collar 710. Therefore, the outer collar 711 is slidable about the inner collar 710.

The outer collar 711 has a rear end 722 which is arranged to locate against the front face 714 of the body 700. A front wall 723 extends inwardly from the front end 724 of the outer collar 711. The front wall 723 has an aperture formed therethrough through which the front section 101 of the injection device is receivable. Recessed sections 725 are formed in the edge of the front wall aperture through which auxiliary cap retaining members 726 are extendable, as will become apparent hereinafter.

Two locking tabs 727, acting as engaging elements, extends inwardly from the inner face 721 of the outer collar 711. The locking tabs 727 are formed diametrically opposite each other. Each locking tab 727 extends from the rear end 722 of the outer collar 711. Each locking tab 727 upstands from the inner face 721 of the outer collar 711. The height of each tab 727, that is the distance between the inner face 721 of the outer collar 711 and the free end of the tab 727 is greater than the radial distance between the inner face 721 of the outer collar 711 and the outer face 715 of the inner collar 710 when the outer collar 711 is rotatably received on the inner collar 710. Each tab is L-shaped with a rear portion and a front portion. The width of the rear portion of each locking tab 727 in an axial direction is equal to or slightly less than the difference in width between the axial length of each cap retaining protrusion 104 and the width of the slot 716 formed in the inner collar 710 between the rear and front edges 717, 718. Therefore, the rear portion of each tab 727 is receivable between the rear edge 717 of each slot 716 and the cap retaining protrusion 104 received therein, as will be explained in detail hereinafter. The width of the front portion of each locking tab 727 in an axial direction is equal to or slightly less than the width of the slot 716 formed in the inner collar 710 between the rear and front edges 717, 718.

Each tab 727 is configured to be received in the corresponding slot 716 in the inner collar 710. Therefore, when the tabs 727 are received in the slots 716, the tabs 727 are slidable along the slots 716 in a circumferential direction. Furthermore, the tabs 727 being received in the slots 716 restricts movement of the outer collar 711 relative to the inner collar 710 and therefore the body 700. When the outer collar 711 is mounted to the inner collar 710, the inner collar 710 is generally hidden from view by the outer collar 711.

A first nodule 735 upstands from the outer surface 715 of the inner collar 710. The first nodule 735 is spaced from the slots 716. A second nodule 736 upstands from the inner surface 721 of the outer collar 711. The first nodule 735 is configured to abut against and locate over the corresponding second nodule 736 when the outer collar 711 is rotated relative to the inner collar 710. The circumferential distance between the tab and the second nodule 736 is slightly greater than the circumferential distance between the first nodule 735 and the corresponding cap retaining member when the cap retaining member is received in the slot.

When the supplementary device is omitted, and the cap 18 is received over the front section 101 of the injection device 1 the cap retaining protrusions 104 locate over one or more retaining elements (not shown) formed on the inner surface of the cap 18 to retain the cap 18 in position over the front section 101. However, it will be understood that in the present embodiment the supplementary device 2 extends partially along the front section 101 of the supplementary device. Therefore, it is not possible for the cap 18 to be retained by the retaining elements. In the present embodiment, the supplementary device further comprises two auxiliary cap retaining members 726 extending from a front end 728 of the inner collar 710.

The auxiliary cap retaining members 726 each comprise a finger 729 and a cap retaining element 730. The fingers 729 of the cap retaining members 726 are spaced from each other to receive the front section of the injection device therethrough. That is, when the fingers 729 are spaced diametrically opposite each other, the distance between the inner surface of the fingers 729 corresponds to the diameter of the front section 101 of the injection device 1. The fingers 729 extend from the front end 728 of the inner collar 710. In the present embodiment, the fingers 729 extend through the recessed sections 725 formed in the front wall 723 of the outer collar 711 when the outer collar 711 is mounted over the inner collar 710. The cap retaining elements 730 are disposed at the free end of the fingers 729.

The cap retaining elements 730 have a height corresponding to the height of the cap retaining protrusions 104. That is, the distance between the inner surface of the fingers 729 and the free edge of the cap retaining elements 730 is the same as the height of the retaining protrusions 104 between the injection device outer surface and the distal free edge of the cap retaining protrusions 104. Therefore, the cap 18 will engage with the cap retaining elements 730 when the fingers are disposed about the outer surface of the front section 101 of the injection device 1. Similarly, the distance between the cap retaining elements 730 and the front wall 723 of the outer collar 711 is equal to the distance between the cap retaining protrusions 104 on the injection device and the shoulder of the injection device 1. Therefore, the cap rim 18a will locate against the front wall 723 of the outer collar 711 when the cap is engaged with the cap retaining elements 730.

To mate the supplementary device 2 on the injection device, the supplementary device 2 is initially located with respect to the injection device. The cap 18 is removed from the injection device 1 and the supplementary device 2 is aligned with the front end of the injection device 1. The body 700 is orientated so that the longitudinal axis of the injection device receiving passage 702 is co-axial with the longitudinal axis of the injection device 1. The supplementary device 2 is received over the injection device 1 so that the injection device is inserted into and received through the passage 702 in the body 700. Therefore, the body 700 acts as a sheath. The body 700 is received over the injection device 1, with the rear end 705 of the body 700 being received over first. The front section 101 of the injection device 1 is able to pass through the front part 707 of the passage 700 due to the front section 101 having a smaller diameter front part of passage 702. The rear section 102 of the injection device 1 is subsequently slid into the passage 102. The rear section 102 is able to slide into the rear part 707 of the passage 702, but is prevented from sliding into the front part 706 due to the rear section 102 of the injection device 1 having a diameter which is greater than the diameter of the front part 706 of the passage 702. Therefore, the shoulder 103 of the injection device 1 abuts against the step 703. Therefore, the step 703 mates with the shoulder 103 and acts as a locating element. At the same point, the locating rib (not shown) is received in the locating channel (not shown) formed in the body. The supplementary device is then correctly orientated with respect to the injection device 1. The step 703 is formed along the supplementary device 2 so that the body 700 is located in a specific position relative to the outer surface 106 of the injection device 1 in a longitudinal direction when the shoulder 103 is received against the step 703.

In the event that the user does not locate the shoulder 103 against the step 703, the rib will not be received in the channel formed in the body. A user would then know that the supplementary device 2 had not mated correctly with the injection pen 1 because the rib would be clearly visible.

As the supplementary device 2 is located over the injection device 1, the user orientates the body 700 of the supplementary device 2 relative to the injection device 1 so that the cap retaining protrusions 104 on the injection device 1 are aligned with the cut-outs 708 formed in the surface of the front part 706 of the passage 702. Therefore, the cap retaining protrusions 104 are able to pass through the front part 706 of the passage 702 and be received in the slots 716 formed in the inner collar 710. When the shoulder 103 locates against the step 703, the cap retaining protrusions 104 locate against the front edge 718 of the corresponding slots 716. The outer collar 711 is initially in its retracted position. That is, the outer collar 711 is rotated with respect to the inner collar 710 so that each tab 727 on the outer collar 711 is rotated away from and spaced from the opening to the cut-outs 708. Therefore, each tab 727 received in its corresponding slot 716 is spaced from the cap retaining protrusions 104. Furthermore, the first nodule 735 on the inner collar 710 is spaced from the second nodule 736.

Figure 28:
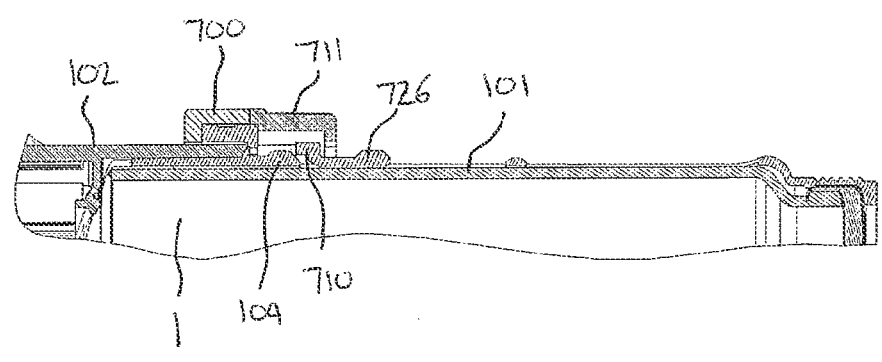
FIG. 28: a cross-sectional side view of the supplementary device shown in FIG. 23 with the injection device of FIG. 1 received through the passage and the securing unit in its retracted position.
Figure 29:
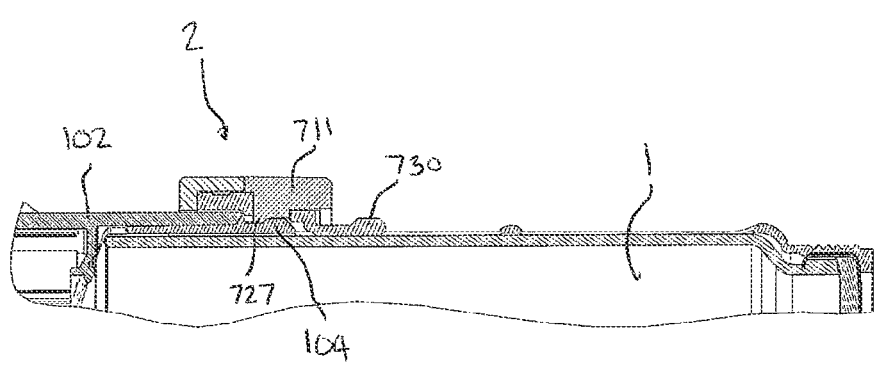
FIG. 29: a cross-sectional side view of the supplementary device shown in FIG. 23 with the injection device of FIG. 1 received through the passage and the securing unit in its secured position.
Figure 30:
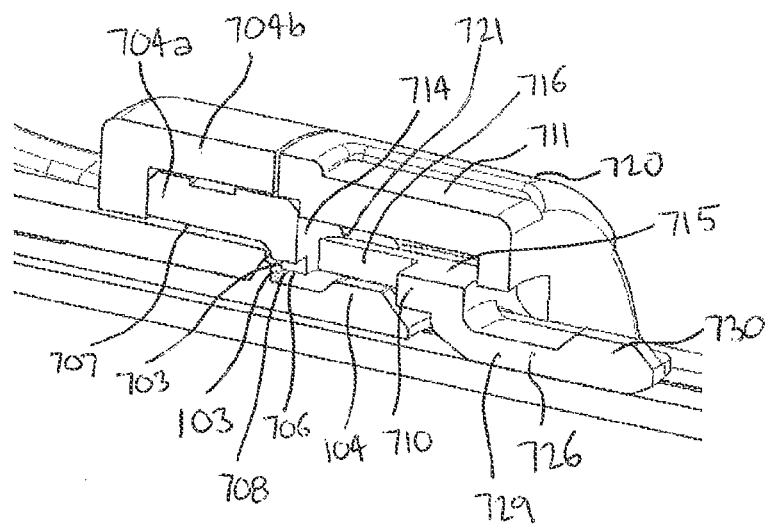
FIG. 30: a partial cross-sectional perspective view of the supplementary device shown in FIG. 23 with the injection device of FIG. 1 received through the passage and the securing unit in its retracted position.
Figure 31:
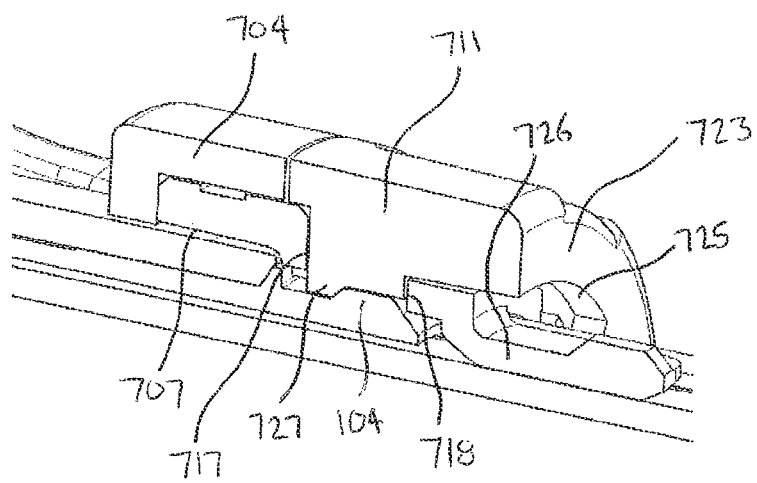
FIG. 31: a cross-sectional side view of the supplementary device shown in FIG. 23 with the injection device of FIG. 1 received through the passage and the securing unit in its secured position.

At this stage, in which the supplementary device 2 is correctly located within the injection device 1, the securing unit 701 is in its retracted position as shown in FIGS. 28 and 30. To move the securing unit 701 to its secured position, as shown in FIGS. 29 and 31, a user separately grasps the body 701 and the outer collar 711. The user then rotates the outer collar 711 relative to the body 710 about the longitudinal axis of the injection device 1 received in the passage 702.

When the outer collar 711 is rotated about the body 701, the outer collar 711 pivots relative to the inner collar 710. The outer collar 711 is rotated in a clockwise direction as seen in FIGS. 30 and 31. Each locking tab 727 slides in its respective slot 716 and is moved towards the cap restraining protrusions 104 received in the slots 716. As rotation of the outer collar 711 continues the rear portion of each tab 727 is received between the cap retaining protrusion 104 and the rear edge 717 of the slot 716. The width of each locking tab 727 in an axial direction is equal to or slightly less than the difference in width between the axial length of each cap retaining protrusion 104 and the width of the slot 716 formed in the inner collar 710 between the rear and front edges 717, 718. Therefore, the locking tabs 727 engage between the cap retaining protrusion 104 and the rear edge 717 of the slot 716. Furthermore, the locking tab 727 obstructs the opening to the cut-outs 708 through which the cap retaining protrusions 104 passed to slide into the slots 716, and so the locking tabs 727 are prevented from sliding back through the cut-outs. Therefore, the cap retaining protrusions are clamped between the front edge of the slots and the rear portion of the locking tabs. Rotation of the outer collar 711 also causes the front portion of each locking tab 727 to move into abutment with the cap retaining protrusions 104. The cap retaining protrusions 104 are therefore clamped in a circumferential direction between the locking tabs 727 and an end of each slot 716.

As the locking tabs 727 move into engagement with the cap retaining protrusions 104, the first nodule 735 upstanding from the outer surface 715 of the inner collar 710 abuts and against the second nodule 736 on the outer collar 711. Further rotational force urges the second nodule to locate over the first nodule. Therefore, the outer collar is retained in its engaged position and the securing unit is retained in its secured position.

A user is then able to locate the cap 18 over the front section 101 and engage the cap with the cap retaining elements 726.

To move the securing unit to its retracted position, a user rotates the outer collar 711 in the opposite direction relative to the body 701.

Although the rib 105 and rib receiving channel aid orientation and location of the supplementary device 2 on the injection device 1 in the above described embodiments, it will be appreciated that in an alternative arrangement the rib 105 and rib receiving recess 318 are omitted and the correct alignment between the supplementary device 2 and the injection device 1 is provided by the step locating against the shoulder.

Other alternative arrangements for ensuring a correct relative position between the supplementary device 2 and the injection device 1 will be envisaged by the skilled person, and all such alternatives are within the scope of the invention except when explicitly excluded by the language of the claims.

It will be understood that clamping surfaces may be integrally formed with each other.

When using embodiments of the present invention, the user inter alia has the following advantages:

The user can use the most convenient disposable insulin injector.

The supplementary device is attachable and detachable (reusable).

The locating unit ensures that the optical sensor is aligned with the dosage window. Therefore, a user does not have to manually orientate the supplementary device.

The securing unit ensures that the supplementary device is securely mounted to the injection device 1. Therefore, the supplementary device does not inadvertently detach from the injection device.

The releasable securing arrangement allows the securing unit to be easily disengaged from the injection device. This allows the supplementary device to be drawn away from the injection device without undue effort from a user. Furthermore, damage to the supplementary device and injection device is prevented during engagement and disengagement of the supplementary device to the injection device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5-des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A supplementary device for a manually operable injection device, the supplementary device comprising
a body defining a passage through which an injection device is longitudinally slidable, the body including a front end having a front face and a rear end, wherein the rear end is configured to be positioned adjacent to a rear end of the injection device; and
a securing unit configured to axially and rotationally secure the body to the injection device in a specific position when the injection device is received through the passage, wherein the securing unit extends from the front face of the body,
wherein the securing unit comprises a collar which is longitudinally movable, relative to the body, between a secured position and a released position,
wherein the securing unit is configured to (i) secure the body to the injection device in the secured position and (ii) release the body from the injection device in the released position.

2. A supplementary device according to claim 1, wherein the passage is an elongate bore formed in the body.

3. A supplementary device according to claim 1, wherein the securing unit comprises at least two clamping surfaces, the securing unit being configured to receive the injection device between the at least two clamping surfaces when the injection device is received through the collar and to bias at least one of the at least two clamping surfaces towards another of the at least two clamping surfaces to clamp the injection device between the at least two clamping surfaces.

4. A supplementary device according to claim 1, wherein the securing unit comprises at least two securing members which are spaced apart to receive the injection device there between, each securing member defining a clamping surface.

5. A supplementary device according to claim 4, further comprising a biasing element configured to bias at least one of the at least two securing members towards the another securing member of the at least two securing members.

6. A supplementary device according to claim 5, wherein the biasing element is the collar extending over the at least two securing members, the collar having a biasing section configured to act on at least one of the at least two securing members to releasably bias at least one of the clamping surfaces towards another clamping surface of the at least two clamping surfaces.

7. A supplementary device according to claim 6, wherein the biasing section is tapered.

8. A supplementary device according to claim 6, wherein the biasing section of the collar is threadingly engaged with the at least two securing members.

9. A supplementary device according to claim 1, wherein the securing unit comprises an engaging element configured to engage with a cap retaining protrusion on the injection device when the body is disposed in a specific position relative to an outer surface of the injection device.

10. A supplementary device according to claim 1, wherein the securing unit comprises an actuating member pivotably mounted in the body having at least one engaging element, the engaging element being configured to engage in an indent on the injection device when the body is disposed in a specific position relative to an outer surface of the injection device and the actuating member is pivoted towards the body.

11. A supplementary device according to claim 1, further comprising a locating unit configured to locate the body in a specific position relative to an outer surface of the injection device.

12. A supplementary device according to claim 11, further comprising an auxiliary cap retaining element configured to releasably retain a cap received over an end of the injection device when the supplementary device is secured to the injection device.

13. A supplementary device according to claim 1, wherein the locating unit comprises a locating step configured to mate with a shoulder formed on the outer surface of the injection device and/or a guide slot configured to mate with a cap retaining protrusion on the injection device.

14. A supplementary device according to claim 1, further comprising an optical reading arrangement and wherein the optical reading arrangement is directed at a display of the injection device when the body is mounted to the injection device in the specific position relative to an outer surface of the injection device.

15. A kit comprising an injection device and a supplementary device according to claim 1.

16. The supplementary device according to claim 1, wherein the securing unit is configured to move axially between the secured position and the released position responsive to rotation of the securing unit relative to the body.

17. The supplementary device according to claim 1, wherein the passage is configured to slidably receive the injection device through the passage in a direction from the front end to the rear end, and the securing unit is at the front end.

18. A supplementary device for a manually operable injection device, the supplementary device comprising:
   a body defining a passage through which an injection device is slidable, the body including a front end having a front face and a rear end, wherein the rear end is configured to be positioned adjacent to a rear end of the injection device;
   a securing unit configured to secure the body to the injection device in a predetermined rotational and axial position when the injection device is received through the passage, wherein the securing unit extends from the front face of the body,
   wherein the securing unit comprises at least two securing members which are spaced apart to receive the injection device therebetween, each securing member defining a clamping surface,
   wherein the securing unit comprises a biasing element configured to bias at least one of the at least two securing members towards the another securing member of the at least two securing members;
   wherein the biasing element is a collar extending over the at least two securing members, the collar having a biasing section configured to act on at least one of the at least two securing members to releasably bias at least one of the clamping surfaces towards another clamping surface of the at least two clamping surfaces, and
   wherein the biasing section of the collar is tapered and is threadingly engaged with the at least two securing members, such that rotation of the collar urges the collar in a longitudinal direction towards the body and urges at least one of the clamping surfaces towards another clamping surface of the at least two clamping surfaces.

19. The supplementary device of claim 18, comprising a locating channel in an inner surface of the passage, the locating channel being shaped to provide a stop that limits axial insertion and rotation of the injection device relative to the body when the body is at a predetermined rotational and axial position relative to the injection device, wherein the locating channel includes a tapered surface configured to engage with a correspondingly shaped locating rib on the injection device to provide the stop.

20. A supplementary device for a manually operable injection device, the supplementary device comprising:
   a body defining a passage through which an injection device is slidable, the body including a front end having a front face and a rear end, wherein the rear end is configured to be positioned adjacent to a rear end of the injection device, wherein the passage extends from a front end to a rear end of the supplementary device, such that when the injection device is received through the passage, the injection device extends from both the front end and the rear end of the supplementary device; and
   a securing unit configured to secure the body to the injection device in a specific position, when the injection device is received through the passage, such that the body obstructs a display window of the injection device, wherein the securing unit extends from the front face of the body;
   a sensor configured to obtain information displayed in the display window of the injection device; and a display device configured to display the information obtained by the sensor.

\* \* \* \* \*

UNITED STATES PATENT AND TRADEMARK OFFICE
CERTIFICATE OF CORRECTION

PATENT NO. : 10,105,094 B2  
APPLICATION NO. : 14/373134  
DATED : October 23, 2018  
INVENTOR(S) : André Baran, Kay Behrendt and Erich Rittenbacher It is certified that error appears in the above-identified patent and that said Letters Patent is hereby corrected as shown below:

On the Title Page

Item (57), Column 2 (Abstract), Lines 1-2, after "device" delete "a supplementary device";

In the Specification

In Column 1, Line 10 (approx.), delete "2013,which" and insert -- 2013, which --.

Signed and Sealed this  
Twenty-ninth Day of January, 2019

Andrei Iancu  
*Director of the United States Patent and Trademark Office*